US008815946B2

(12) United States Patent
Dai et al.

(10) Patent No.: US 8,815,946 B2
(45) Date of Patent: Aug. 26, 2014

(54) INHIBITION OF PROLIFERATION AND FIBROTIC RESPONSE OF ACTIVATED CORNEAL STROMAL CELLS

(75) Inventors: Weixang Dai, Morgantown, WV (US); James L. Funderburgh, Pittsburgh, PA (US); Joel S. Schuman, Pittsburgh, PA (US); Nirmala SundarRaj, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 366 days.

(21) Appl. No.: 12/321,812

(22) Filed: Jan. 26, 2009

(65) Prior Publication Data

US 2009/0239947 A1    Sep. 24, 2009

Related U.S. Application Data

(60) Provisional application No. 61/023,446, filed on Jan. 25, 2008.

(51) Int. Cl.
*A61K 31/22*    (2006.01)
*A61K 45/06*    (2006.01)

(52) U.S. Cl.
CPC ............... *A61K 31/22* (2013.01); *A61K 45/06* (2013.01); *Y10S 514/912* (2013.01)
USPC .......................................... 514/546; 514/912

(58) Field of Classification Search
USPC ................................. 514/546, 912
See application file for complete search history.

(56) References Cited

U.S. PATENT DOCUMENTS

| | | | |
|---|---|---|---|
| 5,033,647 | A | 7/1991 | Smith et al. |
| 5,048,727 | A | 9/1991 | Vlasich |
| 5,108,007 | A | 4/1992 | Smith et al. |
| 5,582,330 | A | 12/1996 | Iba |
| 6,336,571 | B1 | 1/2002 | Chibret et al. |
| 6,432,190 | B1 | 8/2002 | Scholz et al. |
| 6,814,265 | B2 | 11/2004 | Clifford et al. |
| 6,943,190 | B2 | 9/2005 | Fink et al. |
| 2007/0276037 | A1* | 11/2007 | Woo ............... 514/546 |

OTHER PUBLICATIONS

Alam J, Cook JL. How many transcription factors does it take to turn on the heme oxygenase-1 gene? Am J Respir Cell Mol Biol. Feb. 2007;36(2):166-74.

Devamanoharan et al. Attenuation of sugar cataract by ethyl pyruvate, Mol. Cell Biochem. (1999); 200(1-2):103-09.
Ferrari N, Pfeffer U, Dell'Eva R, Ambrosini C, Noonan DM, Albini A. The transforming growth factor-beta family members bone morphogenetic protein-2 and macrophage inhibitory cytokine-1 as mediators of the antiangiogenic activity of N-(4-hydroxyphenyl)retinamide. Clin Cancer Res. Jun. 15, 2005;11(12):4610-9.
Fink MP, Ethyl pyruvate: a novel anti-inflammatory agent J. Int. Med. 2007;261:349-62.
Guerriero et al., Loss of Alpha3(IV) Collagen Expression Associated with Corneal Keratocyte Activation Invest. Ophthalmol. Vis. Sci . . . 2007; 48: 627-635.
Khatari et al., Regulation of Endotoxin-Induced Keratitis by PECAM-1, MIP-2, and Toll-like Receptor 4 Invest. Ophthalmol. Vis. Sci. (2002) 43:2278-2284.
Lin Q, Weis S, Yang G, Weng YH, Helston R, Rish K, Smith A, Bordner J, Polte T, Gaunitz F, Dennery PA. Heme oxygenase-1 protein localizes to the nucleus and activates transcription factors important in oxidative stress. J Biol Chem. Jul. 13, 2007;282(28):20621-33.
Nazarova N, Qiao S, Golovko O, Lou YR, Tuohimaa P.Calcitriol-induced prostate-derived factor: autocrine control of prostate cancer cell growth. Int J Cancer. Dec. 20, 2004;112(6):951-8.
Ohoka N, Yoshii S, Hattori T, Onozaki K, Hayashi H.TRB3, a novel ER stress-inducible gene, is induced via ATF4-Chop pathway and is involved in cell death. EMBO J. Mar. 23, 2005;24(6):1243-55.
Saigusa K, Imoto I, Tanikawa C, Aoyagi M, Ohno K, Nakamura Y, Inazawa J RGC32, a novel p53-inducible gene, is located on centrosomes during mitosis and results in G2/M arrest. Oncogene. Feb. 22, 2007;26(8):1110-21.
SundarRaj, N. et al, MacularCorneal Dystrophy: Immunochemical Characterization Using Monoclonal AntibodiesInvest. Ophthalmol. & Vis. Sci. 28:1678-1686, 1986.
Xu J, Kimball TR, Lorenz JN, Brown DA, Bauskin AR, Klevitsky R, Hewett TE, Breit SN, Molkentin JD.GDF15/MIC-1 functions as a protective and antihypertrophic factor released from the myocardium in association with SMAD protein activation. Circ Res. Feb. 17, 2006;98(3):342-50.

* cited by examiner

*Primary Examiner* — Zohreh Fay
(74) *Attorney, Agent, or Firm* — The Webb Law Firm

(57) ABSTRACT

Provided herein are methods of preventing a fibrotic response and/or scarring in a wound, comprising administering to a subject a composition comprising an amount of an amide or ester of an alpha-ketoalkanoic acid effective to inhibit a proliferative and/or fibrotic response in the wound. In one instance, the wound is to a subject's cornea, such as a wound resulting from refractive surgery. In one embodiment, the amide or ester of an alpha-ketoalkanoic acid is ethyl pyruvate.

8 Claims, 19 Drawing Sheets
(8 of 19 Drawing Sheet(s) Filed in Color)

Control

Scratch wound

Day 1 Post-Wounding

No wound
Stromal thickness 65-67 um
Corneal thickness 131-169 um

LPS alone
Stromal thickness 218-220 um
Corneal thickness 254-258 um
Difficult to estimate

LPS + EP
Stromal thickness 89-100 um
Corneal thickness 194-207 um

Images from Nidek onfoscan 3

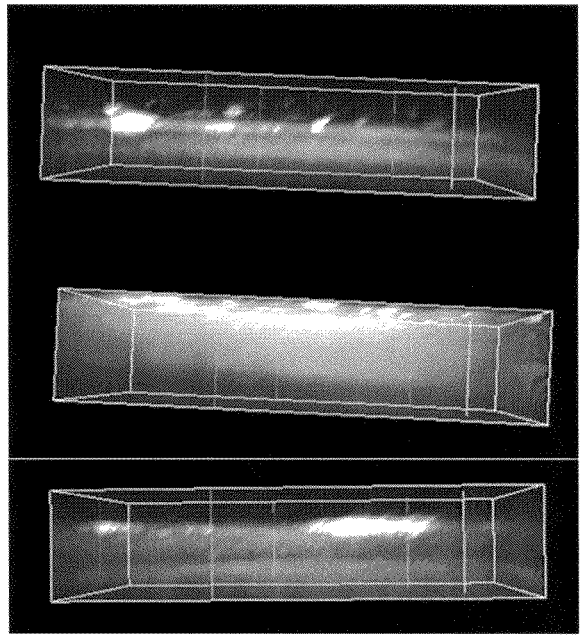

Fig. 13A

Day 2 Post-Wounding

No wound
Stromal thickness 73-82 um
Corneal thickness 151-158 um

LPS alone
Stromal thickness 96-98 um
Corneal thickness 167-169 um

LPS + EP
Stromal thickness 80-85 um
Corneal thickness 142-154 um

Images from Nidek onfoscan 3

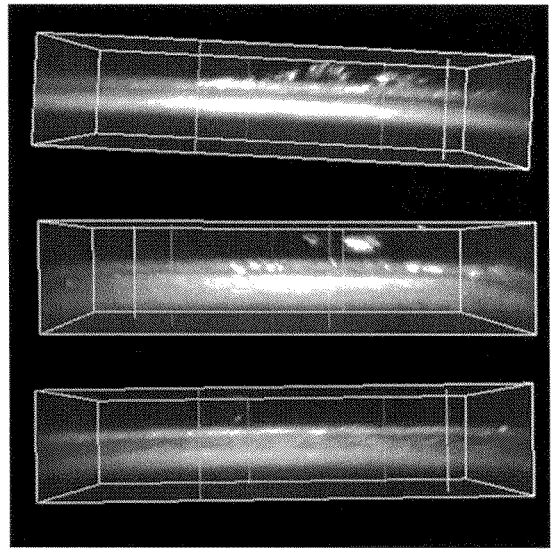

Fig. 13B

Control  15 mM EP

INHIBITION OF PROLIFERATION AND FIBROTIC RESPONSE OF ACTIVATED CORNEAL STROMAL CELLS

CROSS-REFERENCE TO RELATED APPLICATIONS

This application claims the benefit under 35 U.S.C. §119 (e) to U.S. Provisional Patent Application No. 61/023,446 filed on Jan. 25, 2008, which is incorporated herein by reference in its entirety.

SEQUENCE LISTING

A "Sequence Listing" is submitted herewith on compact disc, the contents of which are incorporated by reference in its entirety.

BACKGROUND

Wound healing is a dynamic process that involves many cellular and chemical elements, and results in the rapid sealing of the wound, followed by a longer-term tissue remodeling process in which the wound is healed. Wounds can be caused, without limitation, by mechanical injury, thermal injury, radiation injury or infection. Wounds may occur as a typical part of a surgical or other medical procedure. In many instances, scar formation is a natural result of the wound-healing process due to a fibrotic response. In many instances, scarring as a result of the fibrotic response in wound healing is benign. In other instances, scarring can be undesirable, if not harmful, resulting in scar tissue that is at a minimum, aesthetically displeasing, and at worse, harmful to the function of an organ or biological system in a subject, such as the heart or eye. In most human tissues, a pathological consequence of an inappropriate or poorly regulated tissue repair process is described as fibrosis.

One example of a pathological fibrotic response is the fibrotic response that can occur with corneal injury. In the United States, over 2.4 million people annually experience traumatic eye injuries. Not only are these injuries exquisitely painful when the cornea is involved, but the consequence of improper healing can be debilitating. Also of note, in 2005, an estimated 928,737 Americans underwent refractive surgery. The most common techniques used were LASIK (laser in situ keratomeliusis) or PRK (photorefractive keratectomy). Indeed refractive surgeries are the most common eye surgeries next to cataract extraction. However, manipulation of the cornea involved in these procedures is not without complications, among them being corneal haze, severely dry eyes, undesirable refractive outcomes, and keratitis—all of which could be attenuated by ideal corneal wound healing. An injury to corneal stroma results in activation of corneal keratocytes to proliferative fibroblasts or contractile myofibroblasts, which are often responsible for the development of contractile, nontransparent scar tissue. This outcome is highly undesirable following an injury or refractive surgery. Currently drugs or chemicals, such as mitomycin-C, which are used to prevent cellular activation, proliferation and fibrotic response following corneal or glaucoma filtration surgeries are harsh and can cause irreversible damage to the normal tissue. A less-toxic option for management, for example prevention and/or treatment, of the fibrotic response to corneal injury is desirable. More generally, treatment for the management of the fibrotic response in any tissue is desirable.

SUMMARY

It has now been determined that ethyl pyruvate (EP), as well as other esters or amides of an alpha-ketoalkanoic acid are useful therapeutic agents for treating or preventing proliferative and fibrotic response, for example in the injured eye, and, without limitation in the cornea. Thus, a method of treating or preventing proliferative and/or fibrotic response in a wound in a subject is provided according to one embodiment. The method comprises administering to the subject a composition comprising an amount of an amide or ester of an alpha-ketoalkanoic acid effective to inhibit a proliferative and/or fibrotic response in the wound in a pharmaceutically-acceptable carrier. Also provided herein is a method of modulating gene expression in a corneal stromal cell, comprising contacting a corneal stromal cell with an amide of an alpha-ketoalkanoic acid or an ester of an alpha-ketoalkanoic acid. In certain embodiments, the ester of an alpha-ketoalkanoic acid is chosen from one or more of: ethyl pyruvate, propyl pyruvate, butyl pyruvate, carboxymethyl pyruvate, acetoxymethyl pyruvate, carbethoxymethyl pyruvate, ethoxymethyl pyruvate, 2-oxopropionic acid 3-methoxyphenyl ester, 2-oxopropionic acid 2-ethoxyethyl ester, 2-oxopropionic acid 2-chloroethyl ester, 2-oxopropionic acid isopropyl ester, 2-oxopropionic acid butyl ester, 2-oxopropionic acid p-tolyl ester, 2-oxopropionic acid tert-butyl ester. The wound may be an ocular wound, such as a corneal wound that results from traumatic injury or a surgical procedure such as refractive surgery. The wound also may be a skin wound. Additional active agents, such as an antibiotic agent and an anti-inflammatory agent may be co-administered with the amide or ester of an alpha-ketoalkanoic acid. The amide or ester of an alpha-ketoalkanoic acid may be administered at any time relative to the injury, such as before and/or after the injury.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 13A-13B. Confocal microscopy analysis of the morphology of the corneas after wounding. FIG. 13A shows data day 1 post wounding, where FIG. 13B shows data day 2 post wounding. The images are reconstructed into three-dimensional representations in order to observe gross morphology, measure corneal thickness and light scattering which indicate edema and hypercellularity respectively.

DETAILED DESCRIPTION

Figure 1A:
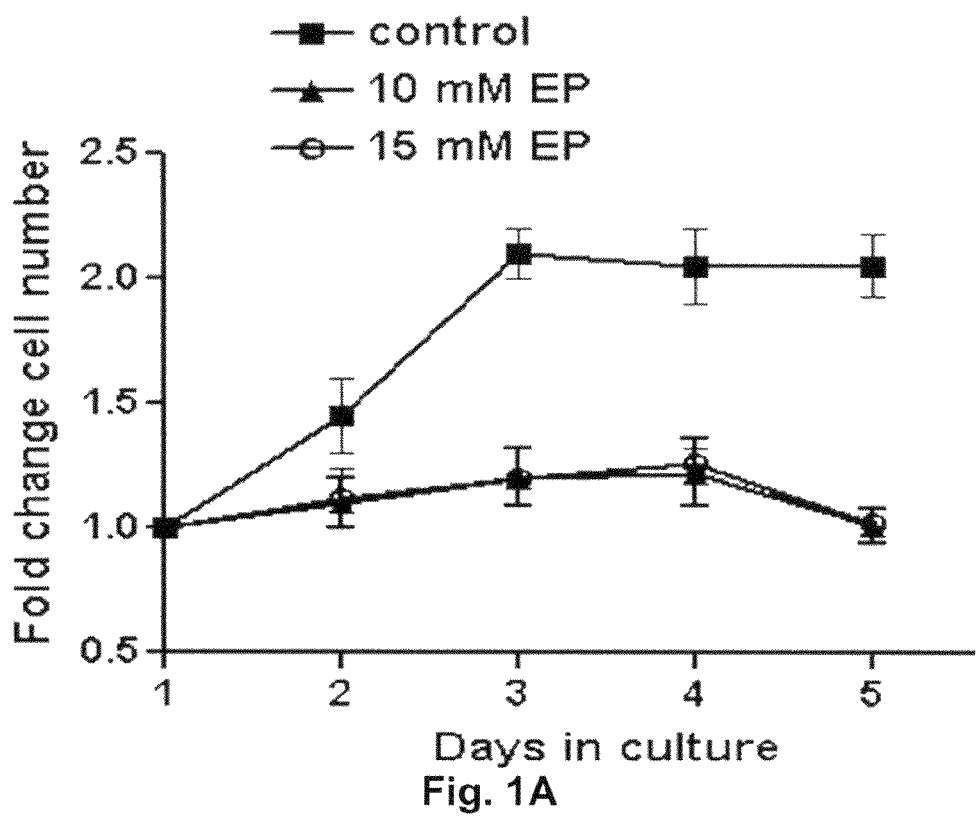
FIGS. 1A-1C. Effect of ethyl pyruvate on the growth of human corneal stromal cells. Corneal stromal cells in P2 growing in DMEM/F12 with 10% FBS were subcultured into desired number of 35 mm tissue culture dishes. After 24 hrs of incubation, the media were replaced with DMEM/F12 medium containing 1% FBS with or without EP (FIG. 1A) or with the same medium containing TGF-β1 or b-FGF/HS with or without EP (FIG. 1B and FIG. 1C, respectively). The cells in several marked regions were counted every 24 hours as described in Methods. The data points are average (±SE) from two separate experiments.

As described herein, compositions and methods for reducing scarring are described. Ethyl pyruvate (EP), as well as other esters or amides of an alpha-ketoalkanoic acid are useful in practicing the methods disclosed, including the use of EP as a therapeutic agent for treating and/or preventing proliferative, fibrotic responses, and leukocyte infiltration, for example in the injured eye, and, without limitation in the cornea.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. All references are fully incorporated by such reference herein, solely to the extent of their technical disclosure and only such that it is consistent with this disclosure.

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used herein, the term "subject" refers to members of the animal kingdom including but not limited to human beings that are treated using the methods and compositions described herein.

"Treatment" of a medical condition associated with a fibrotic response or proliferation or treatment or preventing a fibrotic response or proliferation or scarring means administration to a subject by any suitable route and dosage regimen of a drug product comprising an active agent with the object of ameliorating (e.g., attenuating, alleviating, reducing and/or normalizing) any symptom and/or indicia associated with the medical condition, including, without limitation, any testable parameter, whether or not subjective, such as, without limitation, pain levels, or objective, such as, without limitation, levels of biomarkers in blood sample of a subject, or lesion size. Likewise "treating" such a medical condition may result in amelioration of any symptom and/or indicia associated with the medical condition in a subject.

As used herein, "pharmaceutically-acceptable," means acceptable for use in humans and animals. "Excipients" include, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water. The choice of excipient depends on the dosage form in question. The drug product may be administered, without limitation, intravenously, intramuscularly, orally, topically, intratumorally, intraperitoneally, intrathecally, rectally, vaginally, nasally, optically, buccally, transdermally, subdermally, intradermally, etc., as is appropriate and/or desirable for treatment. Parenteral administration may require at a minimum buffers and salts to match physiological conditions, and thus includes salt and buffer, such as, without limitation, normal saline or phosphate-buffered saline. Depending on the solubility of the compound (active ingredient), the dosage form may be aqueous, micellular (including liposomes) or lipophilic. Formulation of a drug product and choice of suitable excipient(s) with adequate bioavailability is within the average skill of those in the pharmaceutical and formulary arts. The compound may be administered via any useful delivery route, including, without limitation, topically, orally or parenterally, and the drug product/dosage form is tailored to the desired delivery route. For example and without limitation, an HCl salt of a compound described herein may be administered topically, intravenously or intramuscularly in normal saline, or may be administered in tablet or capsule form with appropriate excipients. A large variety of dosage forms are known in the pharmaceutical arts, and many of which may be appropriate for treatment using the methods and compositions described herein (see generally, Troy, D B, Editor, Remington: The Science and Practice of Pharmacy, 21st Edition, Lippincott, Williams & Wilkins (2005)).

In some embodiments, a method is provided of treating or preventing proliferative and fibrotic response in a wound in a subject. The method comprises administering to the subject an amount of an agent comprising an ester or amide of an alpha-ketoalkanoic acid effective to inhibit a fibrotic response in the subject. In one particular embodiment, a method is provided of treating or preventing proliferative and fibrotic response in an eye, and in another embodiment, the cornea of a subject comprising to the subject an amount of an agent comprising an ester or amide of an alpha-ketoalkanoic acid effective to attenuate or otherwise inhibit, but not necessarily completely prevent, activation of corneal stromal keratocyte to myofibroblast phenotype and concomitant cellular proliferation in the cornea and therefore to prevent or minimize scarring of the cornea.

Ethyl pyruvate and certain derivatives are known to attenuate inflammatory responses although the mechanism remains to be fully elucidated. U.S. Pat. No. 6,943,190. However, EP was not known to act on stromal cells. As disclosed herein, ethyl pyruvate and various derivatives thereof, are capable of modulating gene expression in corneal cells directly.

As such, ethyl pyruvate may be used clinically to prevent cell proliferation and fibrosis without causing cell death and/or major tissue damage. This is in contrast to the current methods including use of mitomycin-C, which can be highly toxic. Additionally, EP has favorable pharmacokinetic properties which allows it to diffuse very quickly through the conjunctival tissue or into the corneal stroma. It can enter the anterior chamber within minutes.

In one embodiment, ethyl pyruvate is used to modulate gene expression in a cell. The term "modulate" refers to an increase or decrease (e.g., one-fold, two fold, five-fold, ten-fold, etc.) in expression or activity or one or more genes in response to a stimulus, such as ethyl pyruvate and variations thereof. However, any variation of an alpha-ketoalkanoic acid which can accomplish the same result is envisioned. For example, in one aspect, the alpha-ketoalkanoic acid is an ester of an alpha-ketoalkanoic acid, for example, a C3-C8 straight-chained or branched alpha-ketoalkanoic acid. Examples include alkyl, aryl, arylalkyl, alkoxyalkyl, carbalkoxyalkyl or acetoxyalkyl esters.

In further embodiments, the ester of an alpha-ketoalkanoic acid may include ethyl alpha-keto-butyrate, ethyl alpha-keto-pentanoate, ethyl alpha-keto-3-methyl-butyrate, ethyl alpha-keto-4-methyl-pentanoate, and ethyl alpha-keto-hexanoate. Specific examples include ethyl, propyl, butyl, carbmethoxymethyl ($-CH_2COOCH_3$), carbethoxymethyl ($-CH_2COOCH_2CH_3$), acetoxymethyl ($-CH_2OC(O)CH_3$), carbmethoxyethyl ($-CH_2CH_2COOCH_3$), carbethoxyethyl ($-CH_2CH_2COOCH_2CH_3$), methoxymethyl ($-CH_2OCH_3$) and ethoxymethyl ($-CH_2OCH_2CH_3$). Ethyl esters may be useful in certain instances.

In other embodiments, the ester of an alpha-ketoalkanoic acid may include an alpha-ketoalkanoic acid of the formula $R_1C(O)C(O)OR_2$ wherein $R_1$ and $R_2$ independently comprise an alkyl, aryl, arylalkyl, alkoxyalkyl, alcohol, amine, amide, aromatic, aliphatic, heterocyclic, carbalkoxyalkyl, acetoxyalkyl or combinations thereof. Thus, in some embodiments, $R_1$ and $R_2$ may independently include one or more combinations of functional groups.

In yet other embodiments, the ester of an alpha-ketoalkanoic acid can comprise one or more of: ethyl pyruvate, propyl pyruvate, butyl pyruvate, carboxymethyl pyruvate, acetoxymethyl pyruvate, carbethoxymethyl pyruvate, ethoxymethyl pyruvate, 2-oxopropionic acid 3-methoxyphenyl ester, 2-oxopropionic acid 2-ethoxyethyl ester, 2-oxopropionic acid 2-chloroethyl ester, 2-oxopropionic acid isopropyl ester, 2-oxopropionic acid butyl ester, 2-oxopropionic acid p-tolyl ester, and 2-oxopropionic acid tert-butyl ester.

In still other embodiments, the ester of an alpha-ketoalkanoic acid may comprise a glyceryl ester. As used herein, glycerol esters include glycerol esters of fatty acids, e.g., esters of fatty acids and glycerol or polyglycerol and their derivatives.

In other embodiments, the ester of an alpha-ketoalkanoic acid may comprise dihydroxyacetone esters of the formula $R_1OCH_2C(O)CH_2OR_2$ wherein $R_1$ and $R_2$ independently comprise an alkyl, aryl, arylalkyl, alkoxyalkyl, alcohol, amine, amide, aromatic, aliphatic, heterocyclic, carbalkoxyalkyl, acetoxyalkyl or combinations thereof. Thus, in some embodiments, $R_1$ and $R_2$ may independently include one or more combinations of functional groups. In yet other embodiments, the ester of an alpha-ketoalkanoic acid may comprise a thiolester.

The methods and compositions described herein may optionally employ or include an enolization agent. An "enolization agent" is a chemical agent, which induces and stabilizes the enol resonance form of an alpha-keto ester and may be present in an amount induce to enolization of the alpha-keto functionality, e.g., from 0.0 to 4.0 molar equivalents relative to the ester. Enolization agents include a cationic material, preferably a divalent cation such as calcium or magnesium or, for example, a cationic amino acid such ornithine or lysine.

In other embodiments, the agent includes an amide of an alpha-ketoalkanoic acid. In other embodiments, the agent is an amide of an alpha-ketoalkanoic acid of the formula $R_1C(O)C(O)N(R_2)R_3$, wherein $R_1$, $R_2$ and $R_3$ independently comprise an alkyl, aryl, arylalkyl, alkoxyalkyl, alcohol, amine, amide, aromatic, aliphatic, heterocyclic, carbalkoxyalkyl, acetoxyalkyl or combinations thereof. Thus, in some embodiments, $R_1$, $R_2$ and $R_3$ may independently include one or more combinations of functional groups.

In any case, as used herein, any anti-fibrotic agent used for treating or preventing proliferative and fibrotic response in a wound is administered in an amount effective to inhibit a proliferative and/or fibrotic response in a wound, namely in an amount and in a dosage regimen effective to prevent, reduce the duration and/or severity of the proliferative and/or fibrotic response in the wound such that scarring is reduced. This prevents formation of scar tissue, for instance in a wound, for example, it prevents activation of stromal keratinocytes to form fibroblasts and myofibroblasts in the cornea, in the case of injury to the cornea. Injury resulting in a wound can occur from mechanical injury, from thermal injury, from radiation injury, or from an infection. For example, and without limitation, an eye or corneal wound results from surgical procedures that typically accompany refractive surgery, such as LASIK or PRK surgery, or corneal or glaucoma filtration surgeries. An amount effective to inhibit a proliferative and/or fibrotic response can be determined by any useful method, and can be determined as compared to a negative control in which no active agent is administered, using any effective end-point, such as histochemical, immunohistochemical, nucleic acid expression, or morphological analyses (e.g., formation of scar tissue), and is typically validated by statistical methods.

Non-limiting examples of useful concentrations of ethyl pyruvate or other esters of an alpha-ketoalkanoic acid include from 0.001 mM to 1M, from 0.01 mM to 500 mM, from 0.1 mM and 50 mM, from 1 mM to 25 mM, and from 10 mM to 15 mM, including any ranges and increments of 0.001 mM, 0.01 mM, 0.1 mM, 1 mM, 10 mM, 100 mM, or 500 mM therebetween. In certain embodiments, 10 mM and 15 mM ethyl pyruvate can be effective to prevent activation of stromal cells in the presence of TGF-$\beta$. These useful concentrations are intended end-points for systemic administration as well as useful concentrations for dosage forms to be applied locally, such as, without limitation, topical, ocular, otic, oral (local), suppositories and intravaginal dosage forms, including creams, lotions, ointments, drops, pads, capsules, patches, electrodeposition pads (e.g., iontophoresis), strips, etc.

The active ingredient, esters of an alpha-ketoalkanoic acid, such as ethyl pyruvate, can be administered according to any effective dosage regimen, determinable by any reasonable analysis, such as an animal or human study in which varying doses of the ester of an alpha-ketoalkanoic acid are administered in differing concentrations and/or different dosage regimens to optimize efficacy. Different concentrations of ethyl pyruvate (and its derivatives) and different dosage regimens will achieve similar results, with the drug product administered, typically and without limitation, from one to ten times daily, including 2, 3, 4, 5, 6, 7, 8, 9 and 10 times daily. The amount (e.g., number of drops of drug product for ocular application) of the drug product administered to the subject, also may vary depending on the dosage form (for instance an ocular dispenser) used to administer the drug product and the concentration of the ester of an alpha-ketoalkanoic acid in the drug product. A person of average skill in the pharmaceutical and medical arts will appreciate that it will be a matter of simple design choice and optimization to identify a suitable dosage regimen for treatment and/or prophylaxis In the case of eye or corneal wounds, or other eye wounds, ocular dosage forms include, without limitation, eye drops (liquids), ointments, oils, multi-phase systems (such as, liposome, micellular, homogenates or suspensions of liquids or semi-solid or solid particles), gels, creams, pads or strips. In one embodiment, the active ingredient (drug) is in a water-based (aqueous) drug product. In another embodiment, the active ingredient is in a petrolatum-based drug product. In one embodiment, a combined dosage form is provided comprising an ester of an alpha-ketoalkanoic acid in combination with a second or third active ingredient, such as, without limitation, an anti-inflammatory agent and/or an antibiotic. The dosage form comprises an opthamologically carrier which comprises acceptable excipients, such as, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water, as are broadly known in the pharmaceutical arts.

Also provided herein is a drug product comprising an ocular drug dispenser containing and for delivery of a composition comprising an ester or amide of an alpha-ketoalkanoic acid as described herein, for example and without limitation, ethyl pyruvate. The composition optionally also may comprise an anti-inflammatory agent or antibiotic. A suitable ocular drug dispenser typically is an eye dropper, which typically is a squeezable vial (container) with an integral dropper tip. As is well, known in the art, the structure of the dropper tip, as well as the overall composition of the liquid or hydrogel drug product determines drop size and therefore the dosage regimen appropriate for that dispenser. In another embodiment, the ocular dispenser is an eye cup, facilitating washing of the eye and full contact with a solution. Suitable ocular dispensers are broadly available in the pharmaceutical industry from a variety of specialty manufacturers, and non-limiting examples of which are described in U.S. Pat. Nos. 6,814,265, 6,336,571, 5,582,330, 5,108,007, 5,048,727 and 5,033,647. Further, a survey of commercially-available ocular drug products on the shelves of the average pharmacy illustrates many of the variations such dispensers can take. Of course, the eye dropper per se need not be integral with the vial, but it is useful for control of product sterility. In any case, an ocular drug dispenser is a device useful and acceptable in the pharmaceutical arts for the controlled delivery of a drug product to the eye.

An anti-inflammatory agent may be co-administered in an amount effective to augment decrease of inflammation and pain that may occur in a subject. In the eye, steroidal anti-inflammatory drugs are useful, but can be problematic where they cause corneal thinning and prolong viral shedding. In contrast, non-steroidal anti-inflammatory drugs (NSAIDs) suitable for ocular use include, without limitation: nepafenac (for example and without limitation, Nevenac 0.1%, nepafenac ophthalmic suspension, Alcon Laboratories, Inc.), ketorolac tromethamine (for example and without limitation, Acular LS 0.4%, ketorolac tromethamine ophthalmic suspension, Allergan, Inc.), acetaminophen and bromfenac (for example and without limitation, Xibrom 0.09%, bromfenac ophthalmic suspension, Ista Pharmaceuticals). Thus, also provided herein is a drug product comprising both an ester or amide of an alpha-ketoalkanoic acid and a pharmaceutically acceptable anti-inflammatory suitable for optical use. These anti-inflammatory compounds often exhibit analgesic effects. In any case, according to the methods described herein, the ester or amide of an alpha-ketoalkanoic acid and the anti-inflammatory may be contained in the same composition, but also may be administered separately in a manner effective to treat the infection.

In one non-limiting embodiment, an antibiotic also may be co-administered along with the ester or amide of an alpha-ketoalkanoic acid and, optionally, the anti-inflammatory agent may also be co-administered with the ester or amide of an alpha-ketoalkanoic acid and the antibiotic, all in an amount effective to treat and/or prevent infection. Non-limiting examples of suitable antibiotics for ocular use include: ciprofloxacin, norfloxacin, afloxacin, levofloxacin, gentamicin, tobramycin, neomycin, erythromycin, trimethoprim sulphate, and polymixin B. Other antibiotics/antimicrobials, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscamet, penicillin, ganciclovir, iatroconazole, miconazole, Zn-pyrithione, and silver salts such as chloride, bromide, iodide and periodate, as well as other anti-inflammatory compounds may be included in the drug product comprising the ester or amide of an alpha-ketoalkanoic acid.

The following Examples are provided for illustration and, while providing specific example of embodiments described herein, are not intended to be limiting.

Example 1

In Vitro Model

In the present study an in vitro tissue culture model of growth factor-induced corneal stromal cell activation was employed to evaluate the effects of EP on the phenotypic changes associated with the activation. Corneal keratocytes from human donor corneas or rabbit corneas were cultured in a serum-free medium or in a medium with fetal bovine serum (FBS) for these studies. When the corneal stoma cells are cultured in a serum free medium they retain the phenotype of the quiescent keratocytes in vivo, and when cultured in a medium with low serum (1%) with b-FGF and heparin sulfate (HS) or with TGF-β1 they attain fibroblast and myofibroblast phenotype (wound healing phenotype), respectively.

Ethyl pyruvate, at 10-20 mM concentrations in the medium, inhibited proliferation of human corneal fibroblasts and myofibroblasts. TGF-β1 induced expression of α-SMA, a hallmark of myofibroblast differentiation, was also inhibited by EP as evident from immunocytochemical and Western blot analysis. Activation of keratocytes to myofibroblasts is known to result in increased expression of extracellular matrix proteins including fibronectin, collagen, and other glycoproteins. EP was found to significantly downregulate the expression of fibronectin when rabbit or human corneal stromal keratocytes or fibroblasts were activated with TGF-β1. Microarray analyses indicated that TGF-β1 induced transcription of the genes encoding for fibronectin, tenascin-C and type III collagen and several other ECM components in the corneal stromal cells was downregulated in the presence of EP. The majority of other transcripts which were downregulated by EP in the TGF-β1 activated corneal stromal cells were associated with cell cycle and its control. In conclusion, EP was found to suppress proliferation of corneal keratocytes when activated with growth factors in vitro. EP also downregulated TGF-β1 mediated changes associated with tissue fibrosis in cultures corneal stromal cells. Therefore, EP may have potential clinical application in suppression of undesirable proliferation and scar tissue formation in the cornea or other ocular tissues following surgical procedures or trauma.
Cell Culture and Treatments:
Normal Human Corneal Stromal Cells:

Corneas were dissected from the donor human eyes not usable for transplantation. Using a dissection microscope, the endothelium was removed with forceps and then the epithelium with a thin layer of stroma was removed by making a horizontal cut. The stroma, free of endothelium and epithelium was cut aseptically into small pieces, approximately 1 mm each, and placed onto several 60 mm tissue culture dishes and allowed to dry for 3 minutes. A drop of 1 mg/ml collagenase was then added to each of the explants and after two minutes a sterile coverslip was placed on top of the explants. DMEM/F12 (1:1) medium containing 10% fetal bovine serum (FBS), was added to each dish. The explants were removed after five days and the cells were allowed to grow to confluency. The cells were subcultured using 0.05% trypsin/EDTA. Corneal stromal cells growing in passage 1-3 (P1-P3) in DMEM/F12 were used for studying the effects of ethyl pyruvate (EP).
Normal Human Corneal Stromal Keratocytes:

Corneal stroma, free of endothelium and epithelium as described above, was cut into two halves and then placed into a 35 mm tissue culture dish with serum free DMEM/F12 medium with 0.25 mg/ml collagenase and incubated overnight (37° C., 5% $CO_2$). The dissociated cells were centrifuged at 1200 rpm for 7 minutes. The cells in the pellet were resuspended, centrifuged and then resuspended in 3 ml of serum free DMEM/F12 medium. These cells were passed through a 70 µm cell strainer and plated in Primaria dishes at approximately $6.5 \times 10^4$ cells per dish. After 24 hours the cells were used for activating with specific growth factors (2 ng/ml of TGF-β1 or 20 ng/ml b-FGF/5 µg/ml heparin sulfate) in the presence or absence of EP in DMEM/F12 with 25 mM HEPES.

Cell Proliferation Analysis:

To study the effect of EP on cell proliferation, normal human corneal fibroblasts growing in DMEM/F12 with 10% FBS were subcultured into the desired number of 35 mm tissue culture dishes at a density of $5 \times 10^4$ cells/per dish. After 24 hours of incubation in the above medium, the media were replaced with DMEM/F12 with 25 mM HEPES and 1% FBS (control) or with same medium containing 10 or 15 mM EP. Several regions were marked on the bottom of the dishes and cells in marked regions were counted at 24 hr intervals for five days. Phase contrast digital micrographs of the cells in the marked fields were captured and the cells in the images were counted using MetaMorph® imaging software. The rate of proliferation was evaluated by determining the number of cells at specific time points after treatment/number of cells at the start of the treatment.

Immunocytochemical Analysis:

For immunocytochemical analyses, the cells were cultured on glass cover slips or tissue culture dishes. Cells were rinsed with phosphate-buffered saline (PBS), fixed with paraformaldehyde-lysine-periodate and permeabilized with PIPES buffer containing 0.2% Triton X-100, as described previously (Guerriero et al., *Invest. Opthalmol. Vis. Sci.* 2007; 48: 627-635). Fixed and permeabilized cells were reacted with 10% heat-inactivated goat serum in PBS, pH 7.5, for 45 minutes to block the nonspecific binding of the secondary antibody, rinsed with PBS, and then treated with the primary and secondary antibodies as described previously (Guerriero et al. *Invest. Opthalmol. Vis. Sci.* 2007; 48: 627-635). Primary antibodies included monoclonal rat anti-α smooth muscle actin (SMA) and anti-fibronectin. Secondary antibodies were Alexa 488-conjugated or Alexa 546-conjugated goat anti-rat, anti-rabbit, or anti-mouse IgG at a concentration of 1:1500 for rat and rabbit and 1:2500 for mouse. For double staining of actin filaments, ALEXA™ fluor 546 phalloidin (Molecular Probes) was included at 1:50 dilutions with the secondary antibody. Coverslips with stained cells were then mounted. Fluorescent Z-stack images were collected at 0.25-µm intervals using a confocal scanning laser system attached to an inverted microscope using the same acquisition parameters. The immunofluorescent images were projected from Z-stacks and then digitally processed.

Western Blot Analyses:

Keratocytes or fibroblasts grown under different culture conditions were extracted in RIPA buffer (9.1 mM dibasic sodium phosphate, 1.7 mM monobasic sodium phosphate, 150 mM NaCl, pH, 7.4, 1% Nonidet P-40, 0.5% sodium deoxycholate, 0.1% SDS, 0.03 TIU/mL aprotinin, 1 mM sodium orthovanadate, and 100 µg/mL phenylmethylsulfonyl fluoride (PMSF)). Aliquots of cell extracts containing 50 or 100 µg protein were subjected to SDS-PAGE. Protein bands on SDS-PAGE were electrophoretically transferred to IMMOBILON-P™ membrane (Millipore Corp., Bedford, Mass.), stained with 0.1% Coomassie blue 250 in 40% methanol/1% acetic acid for 1 minute, destained one to three times with 50% methanol/1% acetic acid, scanned for densitometric comparisons of relative concentrations of proteins per lane, destained with methanol, and subjected to Western blot analysis. Immunoreactive bands were detected using chemiluminescence Western chemiluminescence reagents.

Microarray Analysis:

Total RNA was processed and analyzed using the appropriate Affymetrix products (Affymetrix Inc., Santa Clara, Calif.). Eukaryote Poly A RNA internal standards (GeneChip® Poly-A RNA Control Kit from Affymetrix Inc.) were added to the samples, and the mRNA component of the total RNA was reverse-transcribed in the presence of a T7-(dT)24 primer (GeneChip® One-Cycle cDNA Synthesis Kit from Affymetrix Inc.). The resulting cDNA was extracted (GeneChip® Sample Cleanup Module from Affymetrix Inc.) and transcribed in vitro in the presence of biotin-labeled ribonucleotides (Labeling Kit from Affymetrix Inc.). The biotinylated RNA was extracted and fragmented (GeneChip® Sample Cleanup Module from Affymetrix Inc.: 20 µg material fragmented for 35 minutes at 94° C.). Each sample was hybridized overnight to a U133 PLUS™ 2.0 GeneChip (GeneChip® Human Genome U133 Plus 2.0 Array from Affymetrix Inc.). The chips were then washed, developed and scanned in Agilent CHIPSCANNER™ (Affymetrix Inc., Santa Clara, Calif.). Raw data was processed and analyzed using Affymetrix GENECHIP™ Operating System (GCOS) v 1.0.

The U133 PLUS™ 2.0 GeneChips contain 54,675 panels, each targeting a specific transcript sequence. Approximately 20,600 gene products identified by Entrez Gene numbers are redundantly targeted by 46,000 panels: the remaining panels target products which are less well characterized. Affymetrix GCOS™1.0 software was used to assess the presence or absence of the target sequence of each panel. Expression levels were normalized so that the mean for each sample was equal to the global mean for all samples. Panels, which were absent for every sample in either experiment, were omitted from further consideration. This left 23284 panels encoding 12258 unique, characterized (Entrez Gene) genes.

Effect of EP on Cell Proliferation.

Figure 1B:
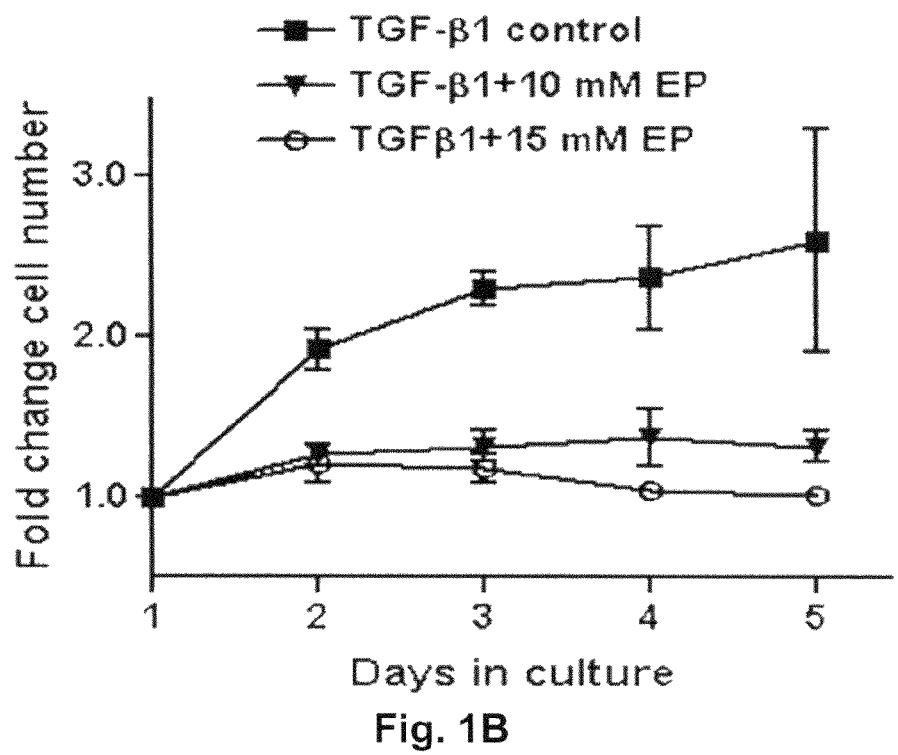
Figure 1C:
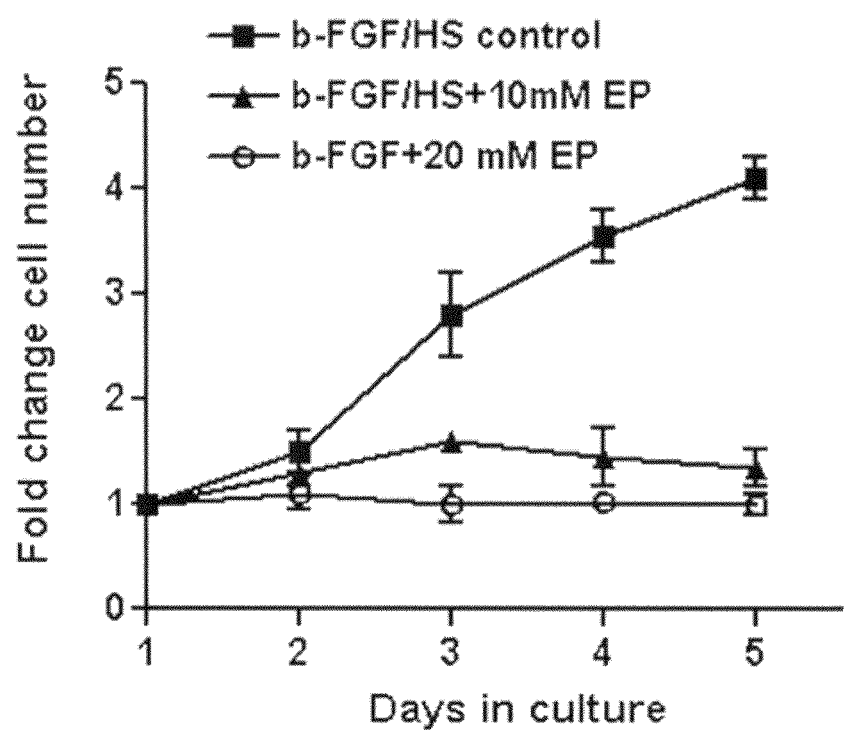

Normal human corneal fibroblasts (between passages 1-3) derived from three different donor eyes were used for studying the effects of EP on cell proliferation as described in the methods. The cells cultured in the presence of b-FGF/HS or TGF-β1 exhibit phenotypic characteristics of in vivo activated corneal stromal cells, fibroblasts and myofibroblasts, respectively, in the wounded stroma. As shown in FIG. 1, when the stromal cells (e.g., fibroblasts) were cultured in media with 1% FBS, with or without TGF-β1 or b-FGF/HS in the presence of 10 mM and 15 mM EP, respectively, there were no significant increases in cell number of TGF-β1 (which induces the cells to myofibroblast phenotype) or with bFGF/HS (which induces the cells to fibroblast phenotype). This result suggested that EP inhibits proliferation of corneal stromal fibroblast and myofibroblast phenotype.

Figure 2:
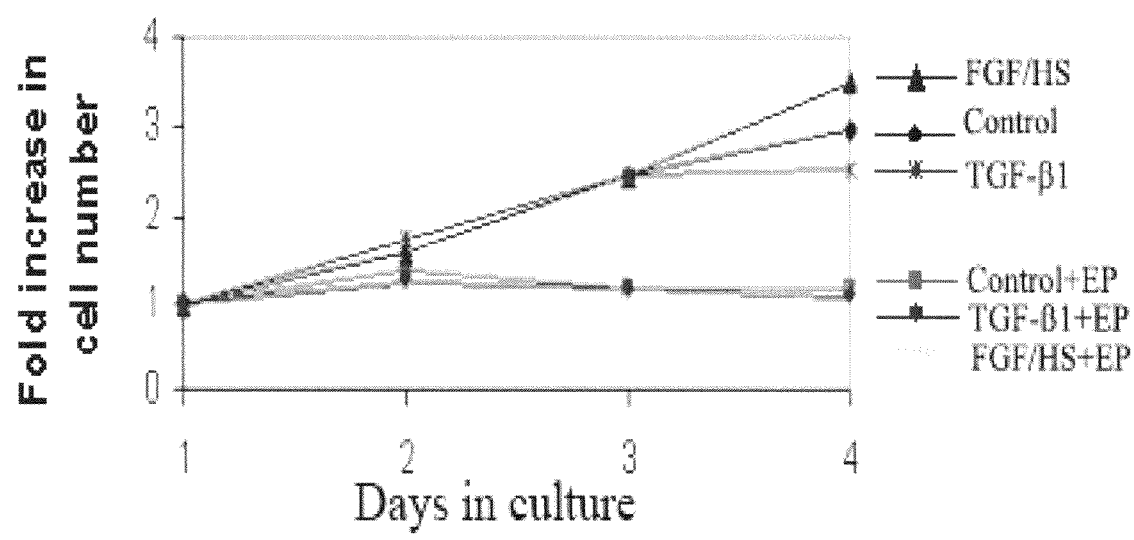
FIG. 2. Effect of ethyl pyruvate on the growth of rabbit corneal stromal cells. Corneal stromal cells in P2 growing in DMEM/F12 with 10% FBS were subcultured into desired number of 35 mm tissue culture dishes. After 24 hrs of incubation, the media were replaced with DMEM/F12 medium containing 1% FBS without EP (labeled "Control"), with EP (labeled "Control+EP"); with the same medium containing TGF-β1 without EP (labeled "TGF-β1") or with EP (labeled "TGF-β1+EP"); or with the same medium containing b-FGF/HS without EP (labeled "FGF/HS") or with EP (labeled "FGF/HS+EP"). The cells in several marked regions were counted every 24 hours as described in Methods. The data presented here are averaged from duplicate sets from a representative experiment.

Because many of the reported studies in the literature have used rabbit stromal cells for in vitro studies on stromal keratocyte activation the effect of EP on proliferation of rabbit corneal fibroblasts and myofibroblasts was also analyzed. As shown in FIG. 2, EP also inhibited proliferation of rabbit stromal cells.

Effect of EP on TGF-β1 Induced Phenotypic Changes in Corneal Fibroblasts:

TGF-β1 is one of the growth factors that are involved in the activation of corneal stromal cells to myofibroblasts, a fibrotic phenotype, during corneal wound healing. Expression of α-SMA is a hallmark of myofibroblast phenotype.

Figure 3:
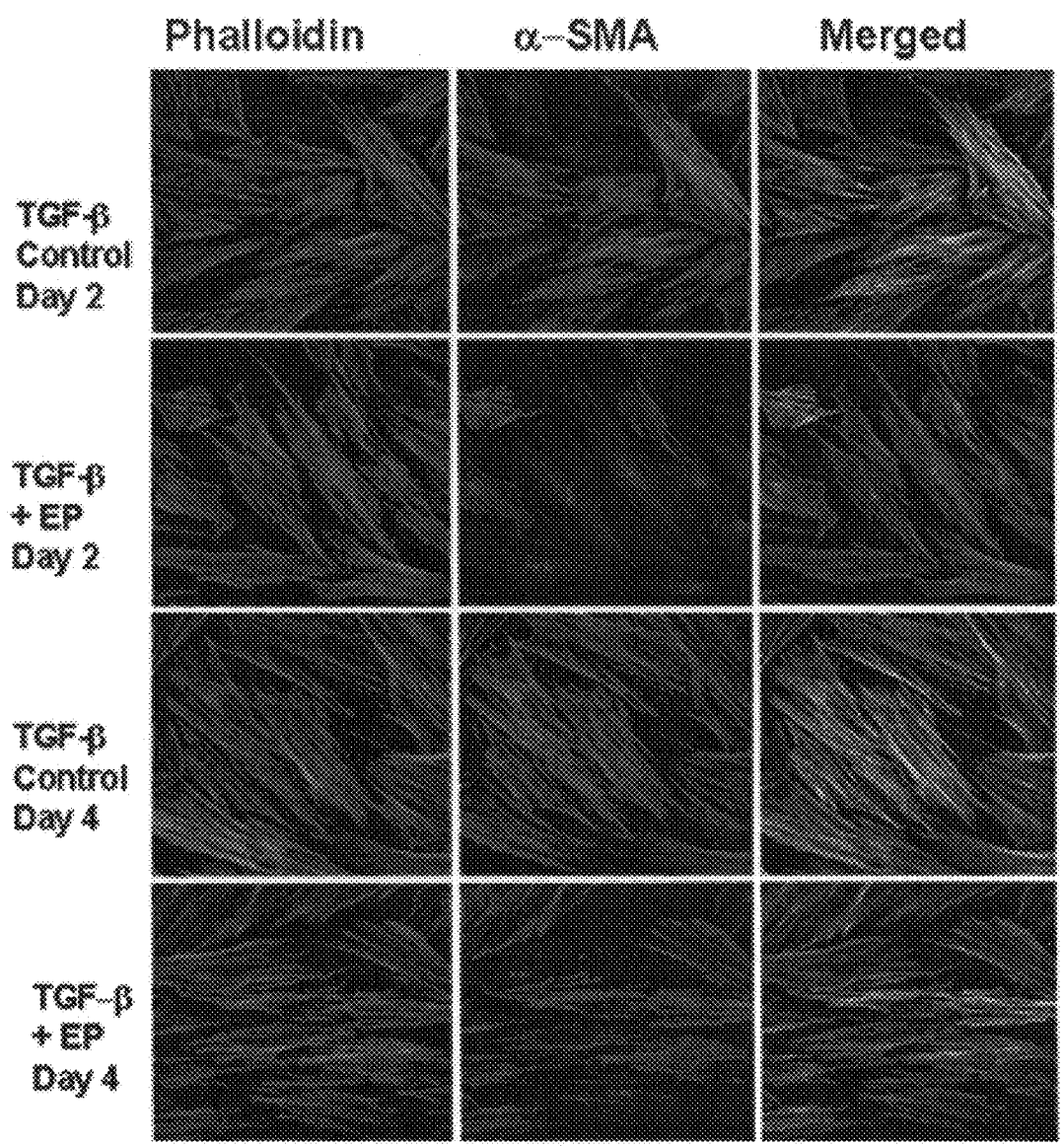
FIG. 3. Immunocytochemical analysis of α-SMA expression. Human corneal stromal cells in P2 growing in DMEM/F12 with 10% FBS were subcultured into desired number of 35 mm tissue culture dishes. After 24 hrs of incubation, the media were replaced with DMEM/F12 medium containing 1% FBS and TGF-β1 with or without (control) 10 mM EP and incubated for two and four days (media were changed every 24 hours). The cells were fixed and double stained for α-SMA (green) and phalloidin (red) using an indirect fluorescence technique as described herein.
Figure 4:
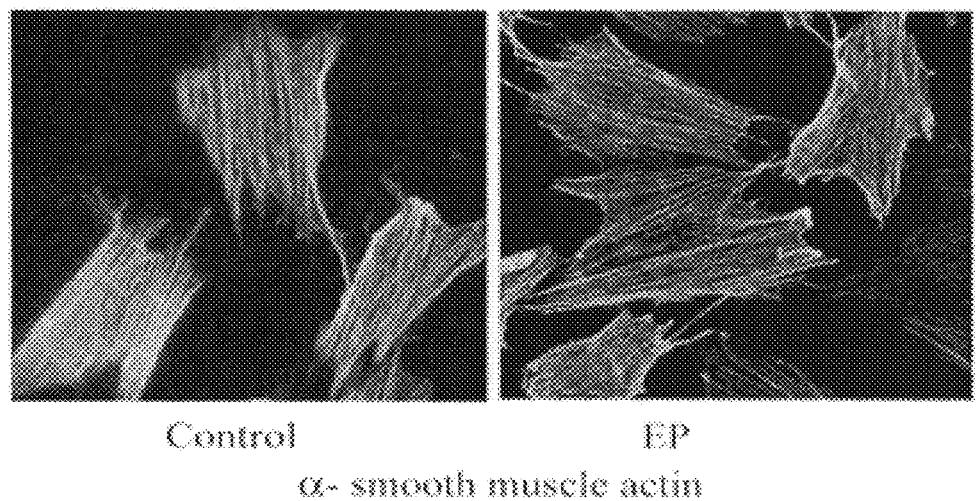
FIG. 4. Immunocytochemical analysis of α-SMA expression. Rabbit corneal stromal cells in P2 growing in DMEM/F12 with 10% FBS were subcultured into 35 mm tissue culture dishes. After 24 hrs of incubation, the media were replaced with DMEM/F12 medium containing 1% FBS and TGF-β1 with or without (control) 10 mM EP and incubated for four days (media were changed every 24 hours). The cells were fixed and stained for α-SMA (green) using an indirect fluorescence technique as described herein.

Other changes include the expression of fibronectin, type III collagen and increased expression of other extracellular matrix proteins including type I collagen and tenascin C. Immunocytochemical analysis indicated that TGF-β1 induced expression of α-SMA was downregulated in the presence of 10 mM EP both in human and rabbit corneal stromal cells (FIGS. 3 and 4, respectively).

Figure 5:
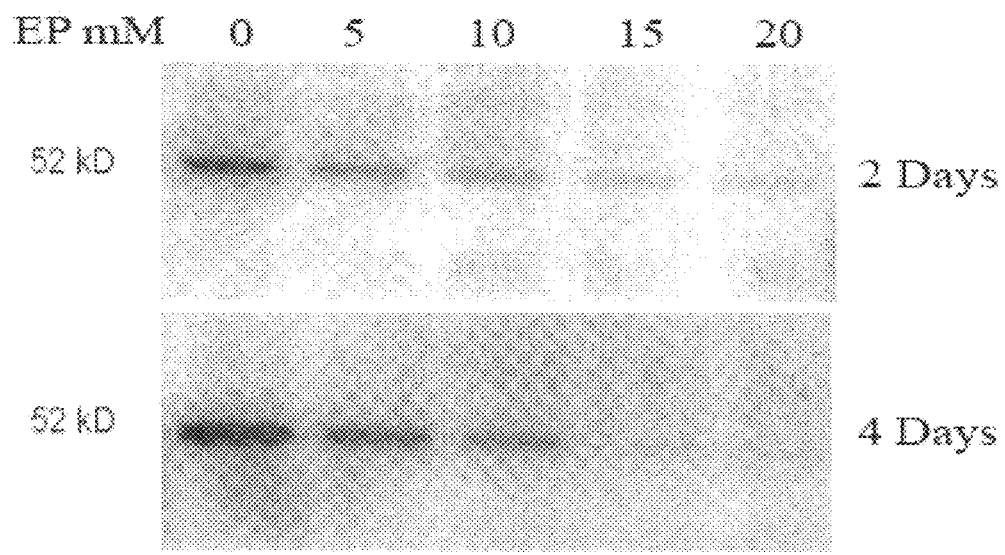
FIG. 5. Western blot analyses of α-SMA. Human corneal stromal cells in P2 growing in DMEM/F12 with 10% FBS were subcultured into 60 mm tissue culture dishes. After 24 hrs of incubation, the media were replaced with DMEM/F12 medium containing 1% FBS and TGF-β1 with or without (control) different concentrations of EP as indicated and incubated for two and four days (media were changed every 24 hours). The cells were extracted in RIPA buffer and the extracts containing 5 μg of total proteins were loaded per lane for Western blot analysis.

Western blot analyses of α-SMA in the total proteins in the extracts of the cells indicated that TGF-β1 induced expression of α-SMA in human corneal stromal cells was downregulated by EP. The inhibition of the expression of α-SMA by EP was concentration dependent (FIG. 5) and the highest downregulation was noted at 20 mM EP. Higher than 20 mM concentrations were toxic to the cells, possibly due to the low pH of the culture medium resulting from high EP concentrations.

Figure 6A:
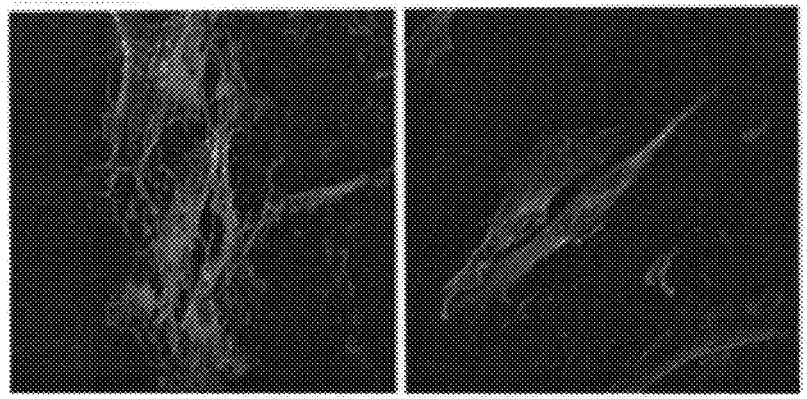
FIGS. 6A-6B. Immunocytochemical analysis of fibronectin expression. Normal human stromal cells (FIG. 6A) or rabbit corneal stromal cells (FIG. 6B) in P2 growing in DMEM/F12 with 10% FBS were subcultured into 35 mm tissue culture dishes. After 24 hrs of incubation, the media were replaced with DMEM/F12 medium containing 1% FBS and TGF-β1 with or without (control) 10 mM EP and incubated for four days (media were changed every 24 hours). The cells were fixed and double stained for fibronectin (green) and phalloidin (red) using an indirect fluorescence technique as described herein.
Figure 6B:
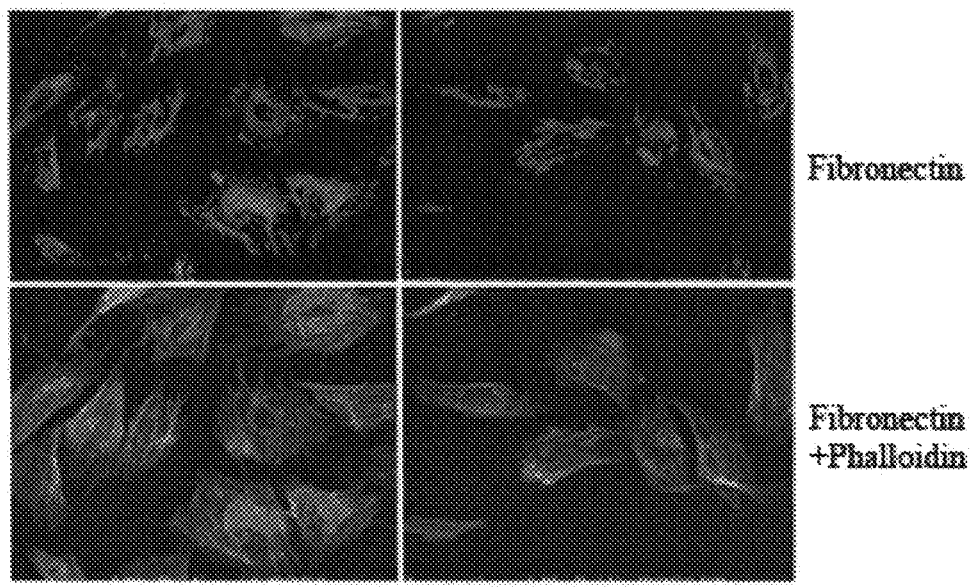
Figure 7:
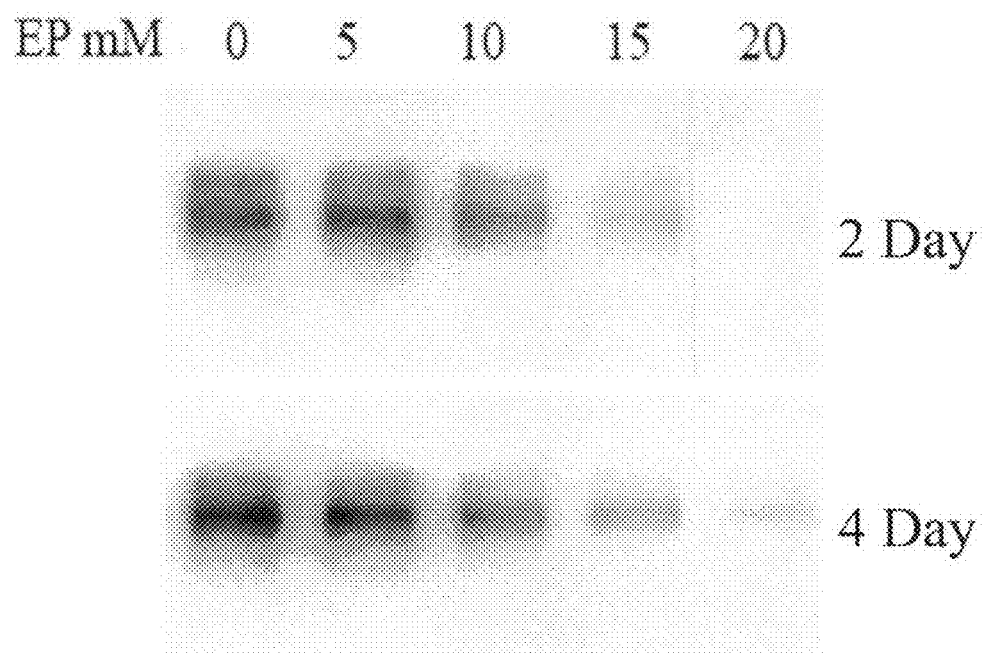
FIG. 7. Western blot analyses of cellular fibronectin. Human corneal stromal cells in P2 growing in DMEM/F12 with 10% FBS were subcultured into 60 mm tissue culture dishes. After 24 hrs of incubation, the media were replaced with DMEM/F12 medium containing 1% FBS and TGF-β1 with or without (control) different EP concentrations as indicated and incubated for two and four days (media were changed every 24 hours). The cells were extracted in RIPA buffer and the extracts containing 5 μg of total proteins were loaded per lane for Western blot analysis.

Similar immunocytochemical analysis indicated that EP induced a concentration dependent downregulation of fibronectin deposition in the matrix of human and rabbit corneal cells treated with TGF-β1 (FIG. 6). This observation was further confirmed by Western blot analysis of the extracts of the cells (including the matrix) as shown in FIG. 7.

Microarray Analysis: Cross-Checking the GeneChip Data.

In earlier work, the changes in the gene expression upon activation of keratocyte to myofibroblast phenotype induced by TGF-β1 was studied. In the present analysis, as a cross check the present, consistent TGFβ-evoked (>2-fold) increases were checked with the previous data. Transition from keratocytes to fibroblasts increased 520 panels, and decreased 700 panels. The 599 unique, characterized genes so altered were compared with a previously acquired database of 873 genes known to be altered by phenotypic transition either from keratocyte to fibroblast or from fibroblast to myofibroblast. The number of genes concordant between these sets was 170, 4.9-fold greater than random chance ($p=1.65\times10^{-130}$, chi-squared test). Extracellular matrix components: 244 panels (143 unique genes) with the Gene Ontology Cellular Component code 5578 (extracellular matrix) were selected. Of these, 28 were TGFβ-1 modulated in the present experiment and 49 were Consistent 5-fold increases in myofibroblasts.

In contrast to the large number of decreases (see below), only four characterized genes are consistently increased 5-fold by ethyl pyruvate in myofibroblasts: response gene to complement 32 or "RGC32" (for example, SEQ ID NO: 1); heme-oxygenase 1 or "HMOX1" (for example, SEQ ID NO: 2); growth differentiation factor 15/NSAID (nonsteroidal anti-inflammatory drug)-activated protein 1/prostate differentiation factor/macrophage inhibiting cytokine-1 or "GDF15" (for example, SEQ ID NO: 3); and tribbles 3 or "TRIB3" or "TRB3" (for example, SEQ ID NO: 4).

Figure 8:
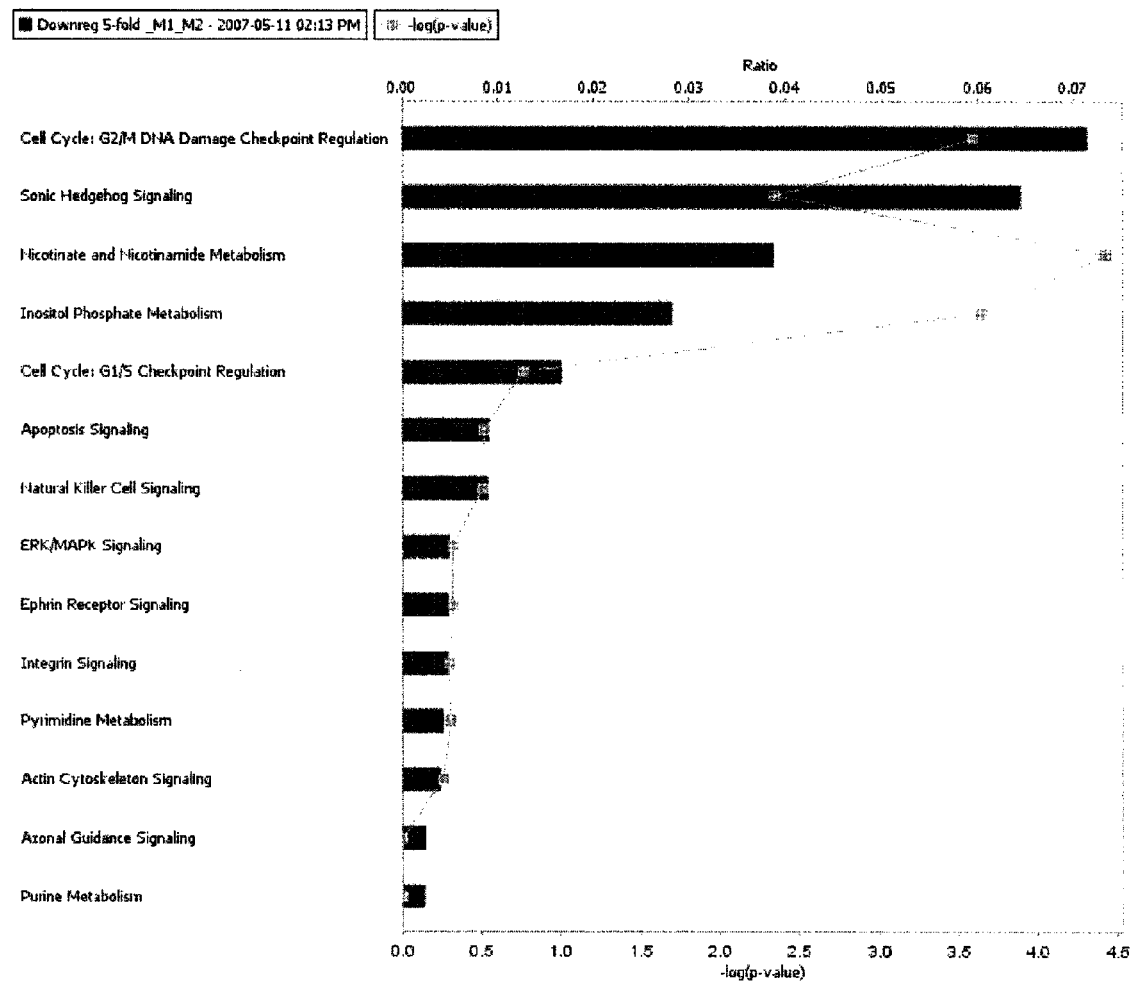
FIG. 8. Ingenuity Pathway Gene Expression Analysis: canonical pathways. The top four functional pathways showed significant enrichment with genes that were consistently decreased 5-fold in myofibroblasts. The most enriched (Cell cycle: G2/M DNA Damage Checkpoint Regulation) is consistent with the decreased proliferation seen on treatment with ethyl pyruvate. Note that Apoptosis Signaling (sixth pathway down) is not significantly enriched (p=0.3). These changes are consistent with the idea that ethyl pyruvate decreases proliferation rather than increasing apoptosis.

Given that the most prominent downregulated group (see FIG. 8) is G2/M DNA damage checkpoint regulation. RGC32 (for example, SEQ ID NO: 1) is of interest because it is a p53-inducible gene whose protein product is located on centrosomes during mitosis and results in G2/M arrest (Saigusa K, Imoto I, Tanikawa C, Aoyagi M, Ohno K, Nakamura Y, Inazawa J RGC32, a novel p53-inducible gene, is located on centrosomes during mitosis and results in G2/M arrest. Oncogene. 2007 Feb. 22; 26(8):1110-21).

Given the known protective effect of ethyl pyruvate against oxidative damage, increased expression of HMOX1 (for example, SEQ ID NO: 2) is of interest since this enzyme is induced by oxidative stress. As Alam and Cook note " . . . members of the heat-shock factor, nuclear factor-kappaB, nuclear factor-erythroid 2, and activator protein-1 families are arguably the most important regulators of the cellular stress response in vertebrates . . . to the best of our knowledge, hmox1 is unique in that it is proposed to be directly regulated by all four of these stress-responsive transcription factors" (Alam J, Cook J L. How many transcription factors does it take to turn on the heme oxygenase-1 gene? Am J Respir Cell Mol Biol. 2007 February; 36(2):166-74). Moreover, heme-oxygenase 1 (for example, SEQ ID NO: 2) is directly protective against oxidative damage, and can localize to the nucleus and activate other transcription factors important in the response to oxidative stress (Lin Q, Weis S, Yang G, Weng Y H, Helston R, Rish K, Smith A, Bordner J, Polte T, Gaunitz F, Dennery P A. Heme oxygenase-1 protein localizes to the nucleus and activates transcription factors important in oxidative stress. J Biol. Chem. 2007 Jul. 13; 282(28):20621-33).

GDF15 (for example, SEQ ID NO: 3) is a member of the TGFβ/BMP superfamily which is antiangiogenic (Ferrari N, Pfeffer U, Dell'Eva R, Ambrosini C, Noonan D M, Albini A. The transforming growth factor-beta family members bone morphogenetic protein-2 and macrophage inhibitory cytokine-1 as mediators of the antiangiogenic activity of N-(4-hydroxyphenyl)retinamide. Clin Cancer Res. 2005 Jun. 15; 11(12):4610-9) antiproliferative (Nazarova N, Qiao S, Golovko O, Lou Y R, Tuohimaa P. Calcitriol-induced prostate-derived factor: autocrine control of prostate cancer cell growth. Int J Cancer. 2004 Dec. 20; 112(6):951-8) and anti-hypertrophic (Xu J, Kimball T R, Lorenz J N, Brown D A, Bauskin A R, Klevitsky R, Hewett T E, Breit S N, Molkentin J D. GDF15/MIC-1 functions as a protective and antihypertrophic factor released from the myocardium in association with SMAD protein activation. Circ Res. 2006 Feb. 17; 98(3): 342-50), all features which would tend to decrease myofibroblast scarring.

TRIB3 (for example, SEQ ID NO: 4) is a cross-over molecule, which interacts with components of multiple signaling pathways. Importantly, TRIB3 (for example, SEQ ID NO: 4) interacts with C/EBP homologous protein (CHOP), which is a stress-inducible nuclear protein crucial for the development of programmed cell death. It has been reported that TRIB3 (for example, SEQ ID NO: 4) downregulates its own induction by repression of CHOP/ATF4 functions and that it is involved in CHOP-dependent cell death during ER stress (Ohoka N, Yoshii S, Hattori T, Onozaki K, Hayashi H.TRB3, a novel ER stress-inducible gene, is induced via ATF4-CHOP pathway and is involved in cell death. EMBO J. 2005 Mar. 23; 24(6): 1243-55). These authors note that "TRB3 could be a sensor for ER stress-induced apoptosis. If the ER stress is transient and mild, the induced TRB3 blocks the CHOP and ATF4 function by binding to them. However, when potent and prolonged ER stress occurs, excess TRB3 will be produced and lead to apoptosis."

Figure 9:
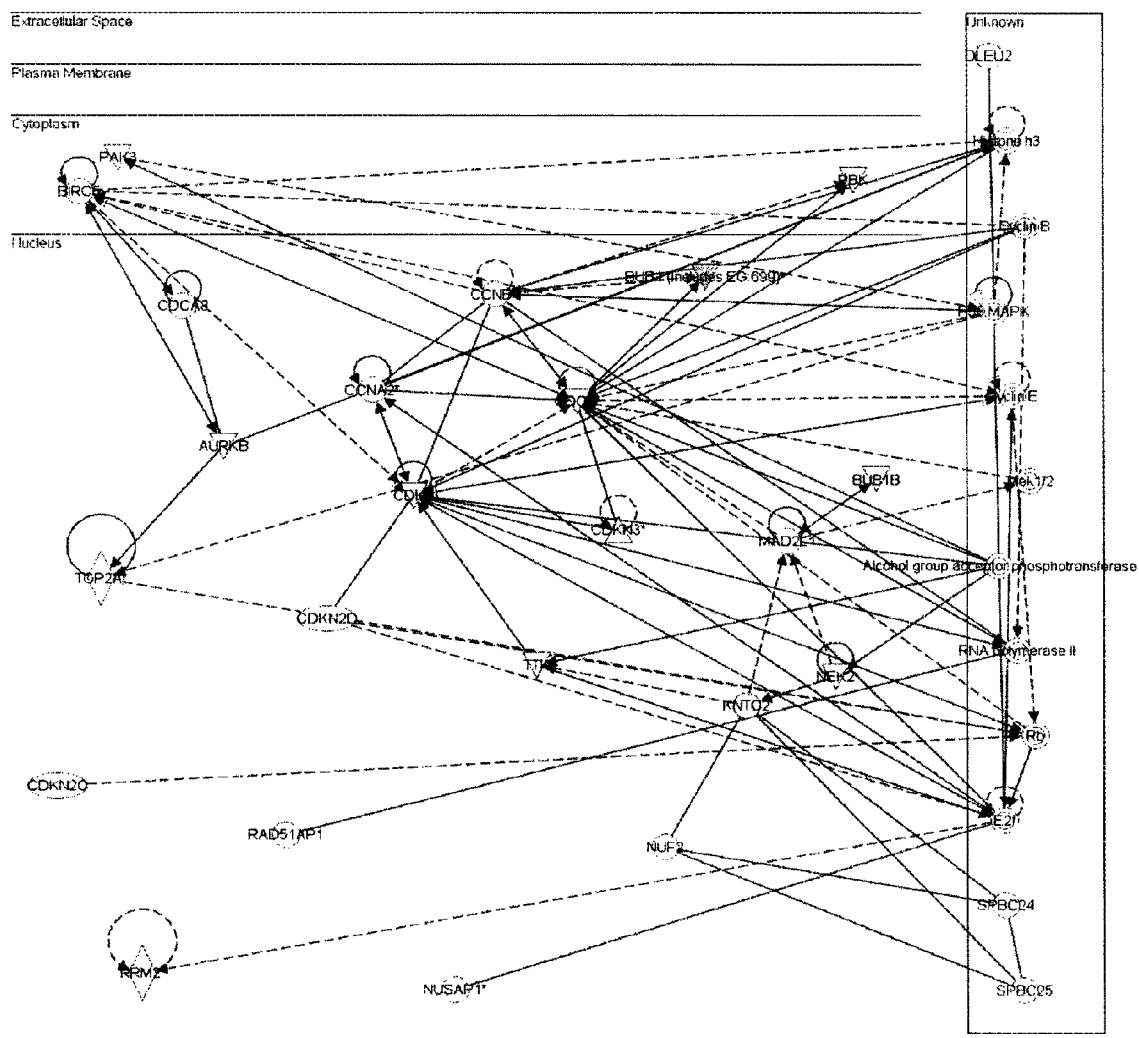
FIG. 9. Network 1 Gene Expression: note the almost exclusive nuclear location of the genes downregulated (shaded). Inferred (unshaded) signaling via p38 MAPK, Mek 1/2 (MAP2K1/MAP2K2) and retinoblastoma protein (Rb).
Figure 10:
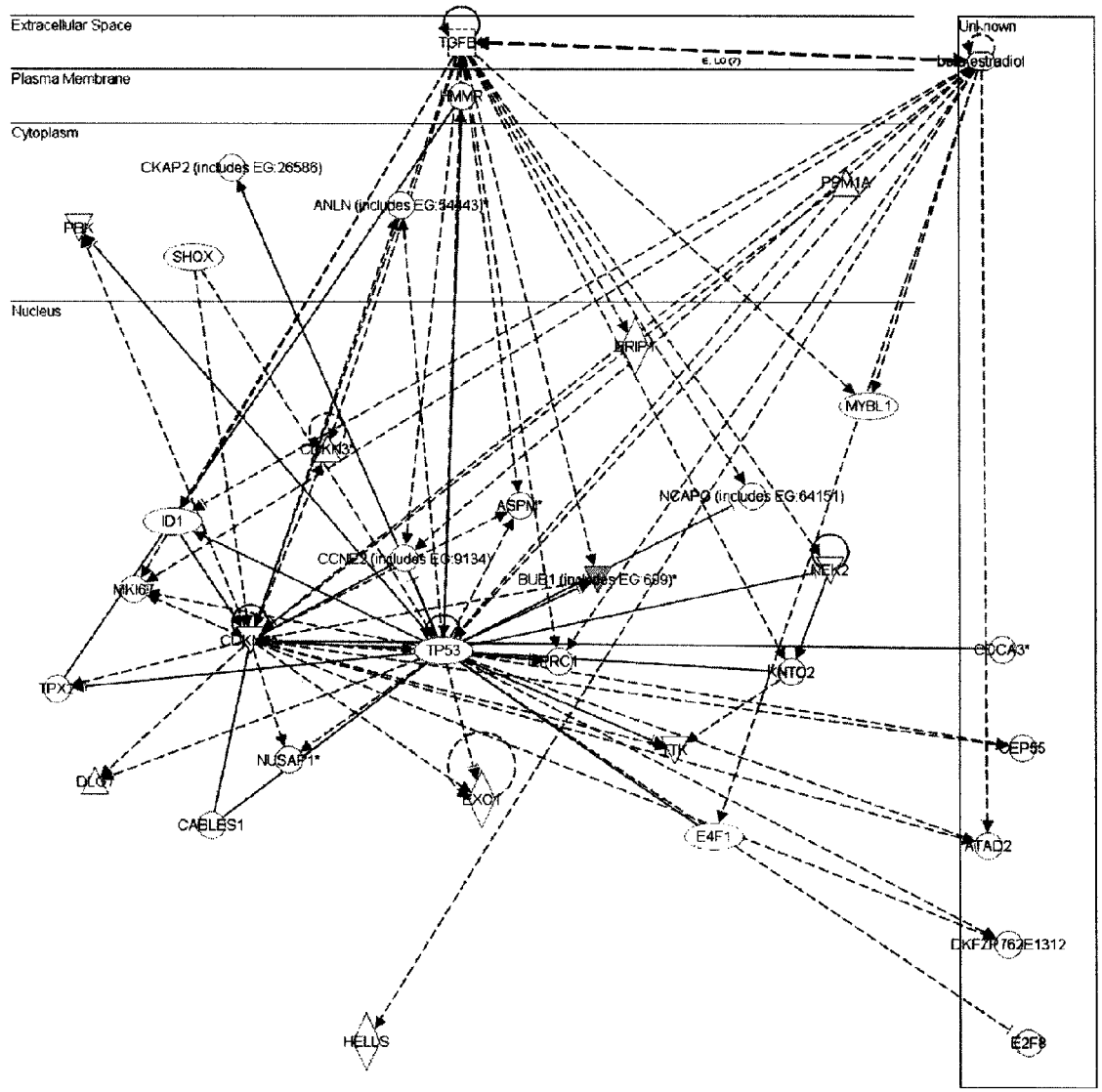
FIG. 10. Network 2 Gene Expression: inferred signaling via tumor protein 53 (TP53), TGF-β and estradiol. Note that the upregulated gene RGC32 is p53 inducible.
Figure 11:
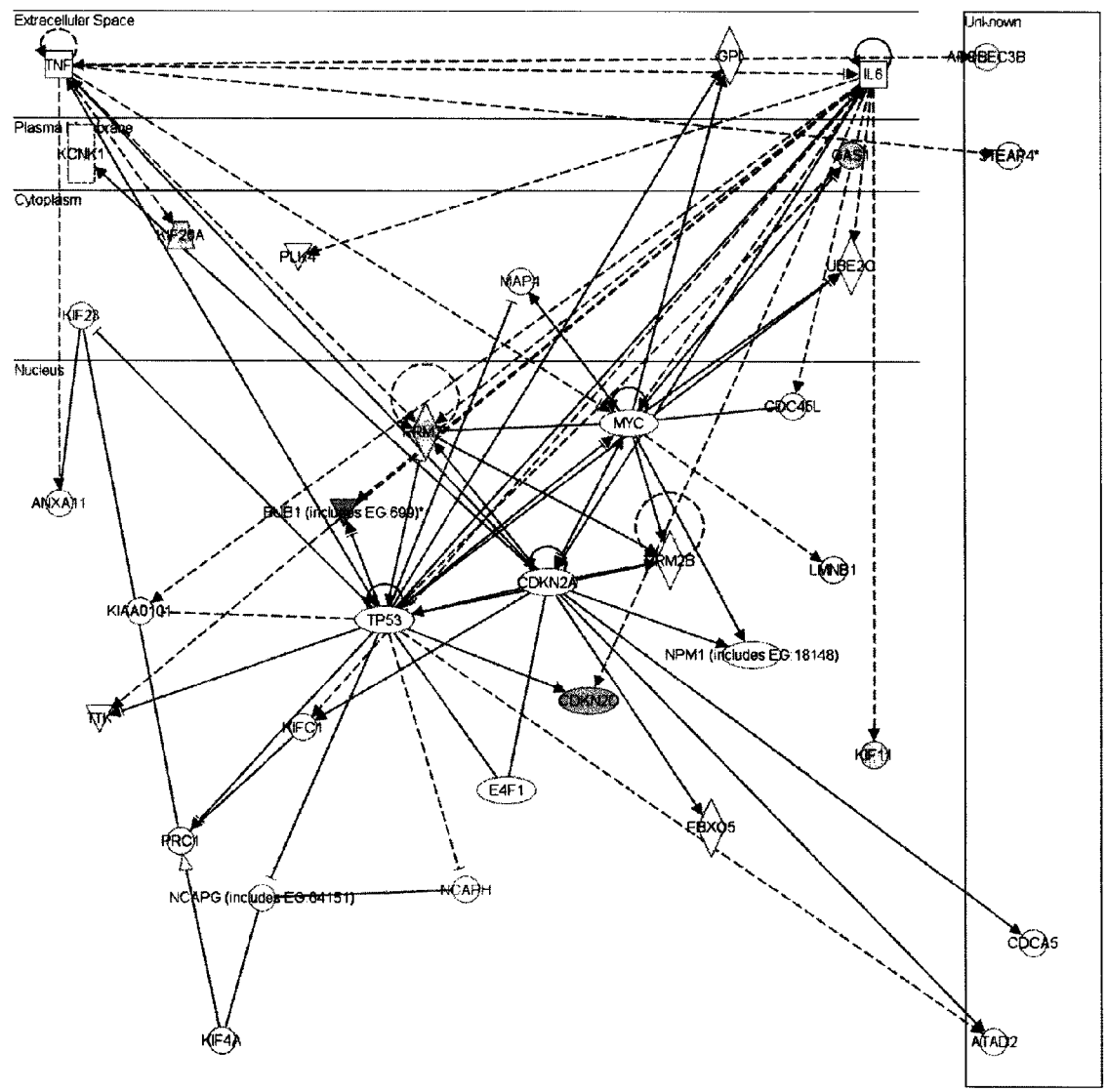
FIG. 11. Network 3 Gene Expression: inferred signaling via tumor protein 53 (TP53), myc, and TNF.

Consistent 5-Fold Decreases in Myofibroblasts:

These comprised eighty-two panels, of which 79 mapped to the IPA database. These panels represented 58 "network eligible" genes which are distributed by function into the groups shown in FIG. 8. These genes also can be parsed into three functional networks with multiple members, and two networks with single members (meiotic nuclear divisions 1 or "MND1" and SHC SH2-binding protein 1 or "SHCBP1", respectively). The three multimember networks (FIGS. 9-11, respectively) showed some overlap between networks 1 and 2 (7 genes) networks 2 and 3 (7 genes) and 1 and 3 (4 genes). In agreement with FIG. 8, the vast majority of genes in all three networks is nuclear in location and is related to cell cycle and its control.

In Table 1 are ECM genes altered by phenotype change, which are also affected by ethyl pyruvate. Genes in bold were altered during phenotype shifts only in previous experiments, genes in italics were altered by phenotype shift only in the present experiment, and genes in normal font were altered by phenotype shifts in both present and prior experiments. An additional 37 genes which showed phenotype shifts in one or more experiments were unaffected (zero, one, or two inconsistent ethyl pyruvate changes).

TABLE 1

Consistent (2-fold) effects of ethyl pyruvate on extracellular matrix genes in 2 phenotypes in 2 independent experiments, i.e. four potential changes

| Two consistent ethyl pyruvate changes | Three consistent ethyl pyruvate changes | Four consistent ethyl pyruvate changes |
|---|---|---|
| collagen, type I, alpha 1 (−2.9) | collagen, type III, alpha 1 (−4.9) | latent transforming growth factor beta binding protein 1 (−4.1) |
| collagen, type I, alpha 2 (−2.7) | collagen, type X, alpha1 (−8.1) | |
| collagen, type V, alpha 1 (−6.2) | laminin, beta 1 (−3.8) | |
| Collagen, type VIII, alpha 1 (−4.0) | matrix metallopeptidase 10 (stromelysin 2) (3.8) | |
| collagen, type VIII, alpha 2 (−3.8) | periostin, osteoblast specific factor (−9.7) | |
| collagen, type XII, alpha1 (−2.8) | secreted phosphoprotein 1 (osteopontin) (2.7) | |
| chondroitin sulfate proteoglycan 2 (versican) (−5.9) | Tissue factor pathway inhibitor 2 (−4.8) | |
| collagen triple helix repeat containing 1 (−4.3) | | |
| EGF-containing fibulin-like extracellular matrix protein1 (−2.6) | | |
| fibronectin 1 (−2.3) | | |
| heparan sulfate proteoglycan 2 (perlecan) (−3.0) | | |
| laminin, alpha 4 (−2.4) | | |
| lysyl oxidase (−4.0) | | |
| matrix metallopeptidase 1 (interstitial collagenase) (5.9) | | |
| secreted protein, acidic, cysteine-rich (osteonectin) (−8.4) | | |
| SPARC-like 1 (−3.3) | | |
| tenascin C (hexabrachion) (−7.4) | | |

Based on the data obtained from the in vitro studies EP clearly shows anti-proliferative effect on activated corneal stromal fibroblasts and myofibroblasts in vitro. Microarray analysis indicates that EP downregulates transcription of many genes that are critical in the cell cycle progression upon direct activation of keratocytes to myofibroblasts in vitro. Therefore, EP likely has a potential application in the regulation of hyperproliferation during corneal wound healing.

Moreover, EP was found to downregulate the expression of α-SMA (a hallmark of myofibroblast phenotype) and expression of fibronectin (an ECM component expressed only in the healing tissues in the cornea). Microarray analysis showed TGF-β1 induced increases in the expression of several other ECM components corneal stromal cells were down regulated by EP. This finding further supports that EP is likely to inhibit scar tissue formation, highly undesirable for the maintenance of corneal structure and transparency. If the observed effects of ethyl pyruvate were not cell type specific, EP will be useful in the prevention of undesirable wound healing response in following surgical procedures.

Example 2

In Vivo Model

Figure 12A:
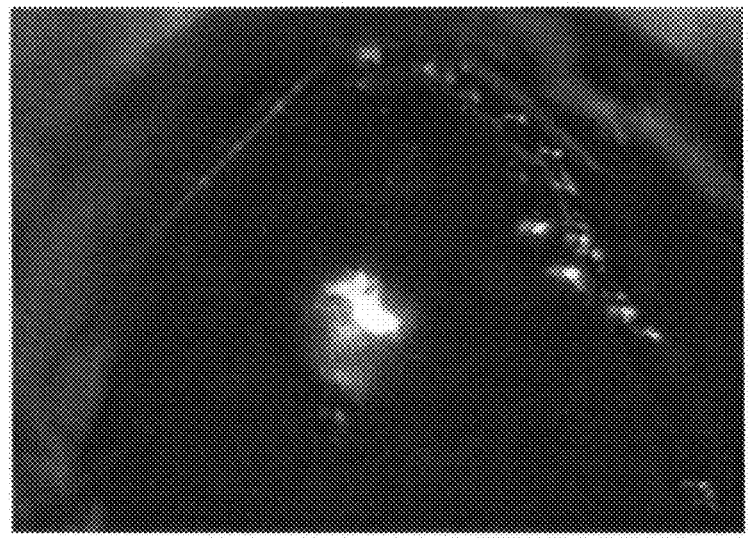
FIGS. 12A-12B. Gross pathology of control (FIG. 12A) and scratch wounding of the eye (FIG. 12B).
Figure 12B:
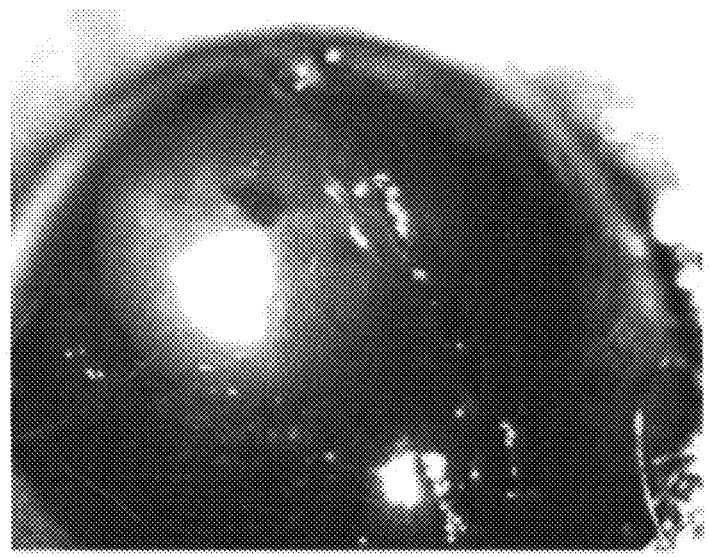

A mouse model of corneal wound healing and inflammation induced by lipopolysacharide (LPS) was used to test the effect of EP. Khatari et al., *Invest. Opthalmol. Vis. Sci.* (2002) 43:2278-2284. Briefly, mice (*Mus musculus* strain C57, age approx. 2 months) were obtained from Charles River Laboratories in accordance with institutional protocols and divided into the following treatment groups (with 3 samples in each group):
a) Unwounded control
b) Wounded control
c) Wound plus EP
d) Wound plus LPS
e) Wound plus LPS and EP Prior to wounding, all mice were anesthetized with an intraperitoneal injection of 50 mg/kg ketamine with 5 mg/kg xylazine. Topical anesthesia was further achieved with an additional 1 drop of 0.5% proparacaine per eye. Once the animal was sufficiently anesthetized, a corneal wound was constructed in each eye using a sterile 26-gauge needle that penetrated the epithelium and the superficial layers of the stroma. This linear scratch extended from the medial to lateral canthus (FIG. 12). 10 μg of the bacterial super-antigen LPS (*Pseudomonas aeruginosa* lipopolysaccharide, Sigma) was applied to the wound using a 10 μl pipette and allowed to penetrate the cornea for 5 minutes. Addition of bacterial endotoxin ensured a robust inflammatory response.

The wound was then washed with phosphate buffered saline (PBS/non-pyrogenic $dH_2O$). Following the wash, the EP treatment groups received a 10 μl drop of 5% EP in PBS buffered to physiological pH with HEPES while the control group received PBS alone. Drops were applied to the corneal wound using a pipette and the mice were held by hand in such a way as to retain the drops on the eye for approximately 2 minutes. The delivery and concentration of EP was determined according to Devamanoharan et al. (1999); 200(1-2): 103-09. When applied on the surface of the eye, EP has been shown to diffuse into the aqueous humor within 15 minutes. Considering this quick absorption with the elimination half-life of EP, which is approximately 90 minutes, EP (500 mM) was applied every 90 minutes over the span of 12 hours during each day, followed by 12 hours of treatment overnight.

Animals were sacrificed and eyes harvested for analysis at 1 and 2 days post-wounding. After sacrificing, but prior to harvesting, eyes were imaged using the NIDEK CONFOSCAN 3® confocal microscope to analyze the morphology of the intact cornea. The images were later reconstructed into three-dimensional images in order to observe gross morphology, measure corneal thickness and light scattering which indicate edema and hypercellularity respectively.

At 1 day post-wounding, control (unwounded, untreated) corneas had a normal stromal thickness ranging from 65-67 μm with a total corneal thickness of 131-169 μm (FIG. 13). Wounded corneas treated with LPS alone had a significantly larger stromal thickness of 218-220 μm, with total corneal thickness 254-258 μm (FIG. 13). The stromal thickness in the LPS group was difficult to measure due to significant light scattering and destruction of the normal morphology that allows the visual discrimination between cell layers. The EP treatment mitigated post-wounding edema as indicated by a smaller stromal thickness of 89-100 μm with total corneal thickness ranging from 194-207 μm (FIG. 13). Qualitatively, whereas the LPS treated group showed significant light scattering within the stromal layer, the EP treatment group while still having an overall thicker cornea compared to unwounded control, still exhibited a dark and quiet stroma in contrast to the wounded corneas not treated with EP.

After 2 days post-wounding, both untreated and EP-treated wounded corneas were thinner with morphology more similar to their unwounded counterparts showing that in both groups the wounds was beginning to heal and edema was resolving (FIG. 13). The EP treated group exhibited a stromal thickness of 80-85 μm and total corneal thickness 142-154 μm and the untreated wounded group was comparable with a stromal thickness of 73-82 μm and total corneal thickness 151-158 μm. This is compared to the 2-day unwounded control stromal thickness of 73-82 μm and total corneal thickness 151-158 μm. The stark contrast between the EP-treated and untreated wounded corneas, however, was that the untreated wounded corneas showed significantly more light scattering within the stromal layer even after edema was appearing to resolve, while the EP treated corneas were again normal in morphology.

After imaging, corneas were processed to harvest the cells and cells were immunostained for the following inflammatory cell markers and subjected to flow cytometry (FACS) analysis: GR-1—a neutrophil marker, and CD-45+—a pan-leukocyte marker. Wounded controls were used for the appropriate isotype controls for the above markers.

One whole eye from each treatment group was embedded in mounting media for cryosectioning and immunostaining. The stained whole corneas were examined by fluorescence and confocal microscopy and digital images were captured for quantitative image analyses using METAMORPH™ imaging software. Immunostaining included stains for the following fibrotic markers: alpha-smooth actin—a marker of the myofibroblast phenotype to identify activated stromal cells, Ki-67—a proliferative nuclear antigen to identify proliferating cells in G1/S, and Type III collagen, fibronectin and tenascin C—extracellular matrix proteins which are components of the scar tissue expressed in response to wounding.

Figure 14A:
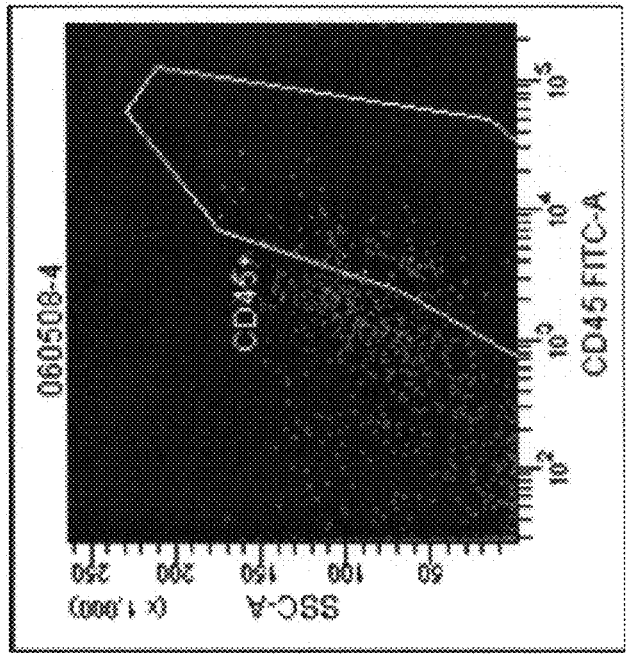
FIGS. 14A-14B. FACS analyses using the pan-leukocyte marker CD-45+ showing that in the control non-wounded cornea less than 0.2% of the cells comprised leukocytes at day 1 (FIG. 14A) and day 2 (FIG. 14B).
Figure 14B:
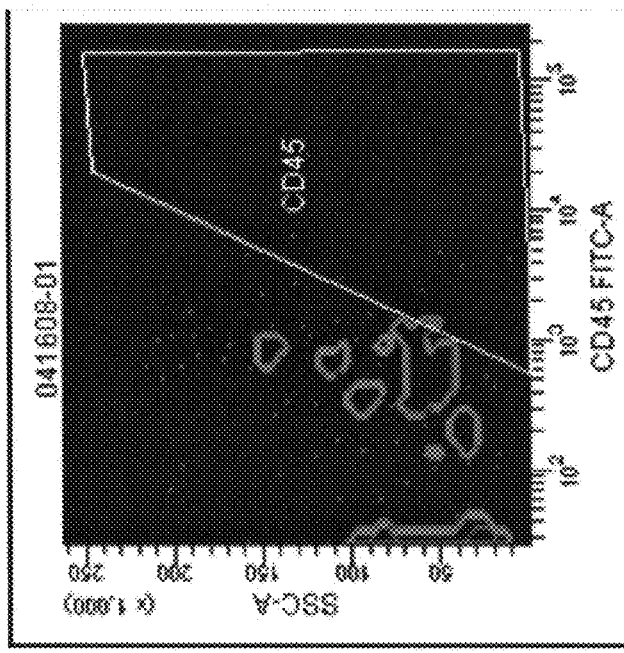
Figure 15:
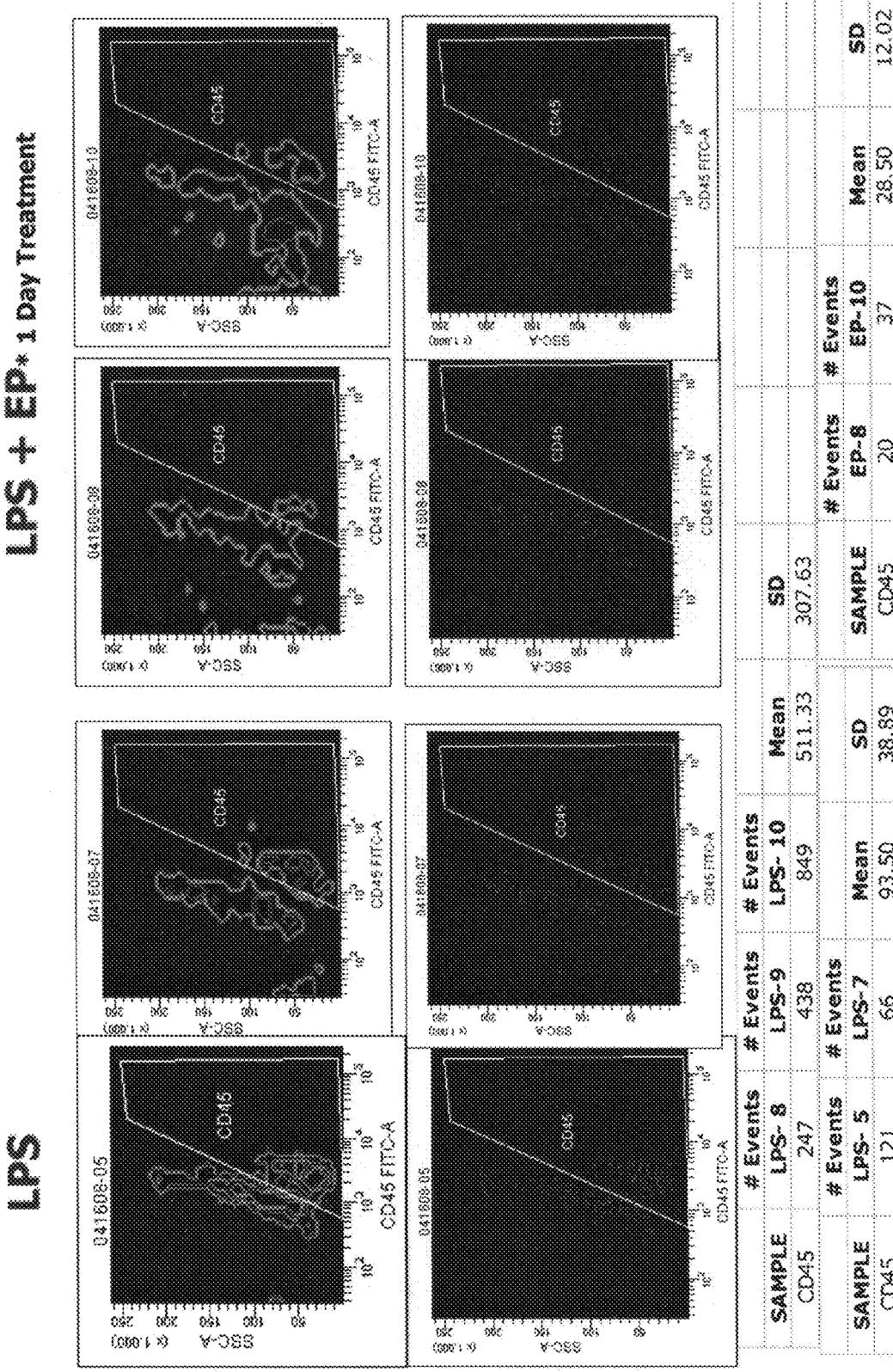
FIG. 15. FACS analyses using the pan-leukocyte marker CD-45+ at day 1 post-wounding showing significantly fewer inflammatory cells in the EP treated group compared to wounded, untreated controls. (28.50±12.02 compared 93.50±38.89, respectively).
Figure 16:
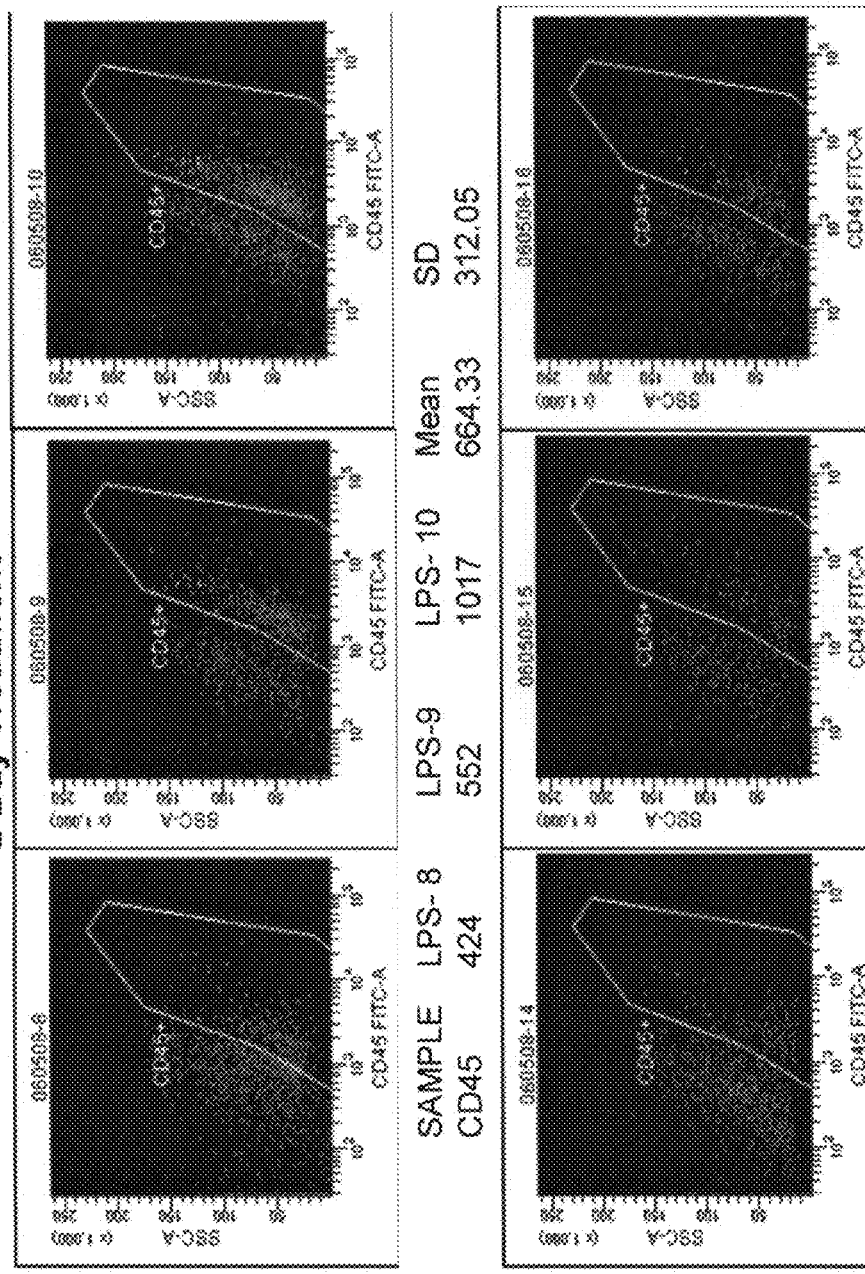
FIG. 16. FACS analyses using the pan-leukocyte marker CD-45+ at day 2 post-wounding showing significantly fewer inflammatory cells in the EP treated group compared to wounded, untreated controls (163.00±57.42 compared to 664.33 SD±312.05).
Figure 17:
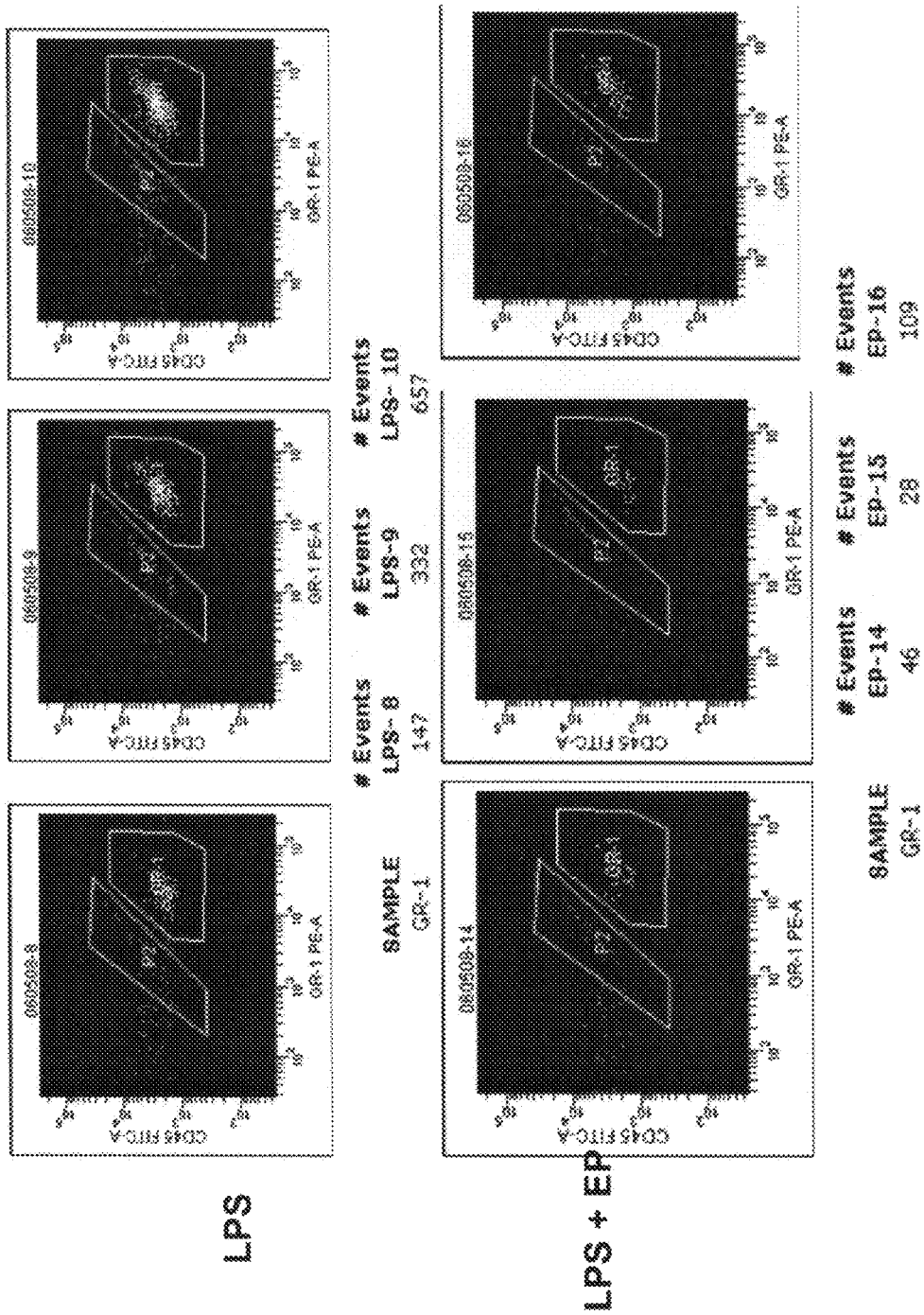
FIG. 17. FACS analysis using neutrophil marker GR-1 showing that neutrophils comprised approximately 57% of the infiltrated leukocytes at day 2 days post-wounding. Significantly fewer neutrophils are present in the EP treated group compared to wounded, untreated controls (61.00±42.53 vs. 378.67±258.18).

EP treatment also suppressed the migration of inflammatory cells to the wound site. FACS analyses using the pan-leukocyte marker CD-45+ showed that in the control non-wounded cornea less than 0.2% of the cells comprised leukocytes (FIG. 14). At day 1 post-wounding, flow cytometry analysis showed significantly fewer inflammatory cells in the EP treated group compared to wounded, untreated controls. (28.50±12.02 compared 93.50±38.89 respectively) (FIG. 15). Similarly at day 2 post-wounding, FACS analysis using the pan-leukocyte marker CD-45+ showed significantly fewer inflammatory cells in the EP treated group compared to wounded, untreated controls (163.00±57.42 compared to 664.33 SD±312.05) (FIG. 16). FACS analysis using neutrophil marker GR-1 indicated that neutrophils comprised approximately 57% of the infiltrated leukocytes at day 2 days post-wounding (FIG. 17). Significantly fewer neutrophils were present in the EP treated group compared to wounded, untreated controls (61.00±42.53 vs. 378.67±258.18).

Example 3

Ethyl Pyruvate Derivatives In Vitro

After determining that ethyl pyruvate downregulates the TGF-β1 induced fibrotic phenotype of corneal stromal cells in culture, several derivatives of ethyl pyruvate were analyzed for their effects on b-FGF or TGF-β1 induced changes in corneal stromal cells As described in Example 1, corneal stromal cells were isolated from rabbit corneas and cultured using the same procedures. The keratocytes in serum free media were treated with b-FGF (40 ng/ml)+HS (5 μg/ml) with or without 15 mM EP or 1, 2.5 or 5 mM following EP derivatives: 2-oxopropionic acid 3-methoxyphenyl ester, 2-oxopropionic acid 2-ethoxyethyl ester, 2-oxopropionic acid 2-chloroethyl ester, 2-oxopropionic acid isopropyl ester, 2-oxopropionic acid butyl ester, 2-oxopropionic acid p-tolyl ester, 2-oxopropionic acid tert-butyl ester. Two days following the treatments, the cells were fixed and stained for Ki67 (a nuclear antigen expressed during the G1/S or S phase of the cell cycle) as described supra. The relative levels of the expression of specific proteins were analyzed by Western blot analyses of the cell lysates as described supra.

Figures 18A, 18B:
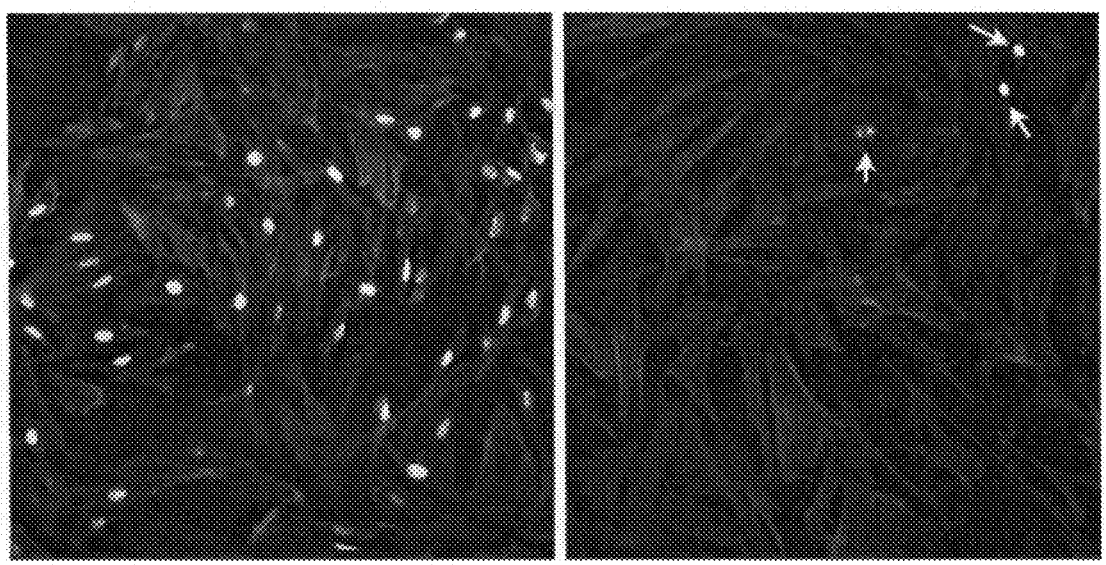
FIGS. 18A-18B. Rabbit corneal keratocytes were activated with bFGF (40 ng/ml)+HS (5 μg/ml) without EP (FIG. 18A) or with 15 mM EP (FIG. 18B) and after two days the cells were triple stained with anti-Ki67 antibodies (yellow), phalloidin (red, actin filaments) and DAPI (blue, nucleus). Note only a few Ki67 positive cells in EP treated cultures.

Ethyl pyruvate treatment of corneal stromal cells activated with b-FGF or TGF-β1 results in the inhibition of the reentry of cell in the S phase (DNA synthesis) as evident from diminution of the cells expressing Ki67 to less than 1% (FIG. 18). Of the seven ethyl pyruvate derivatives listed above 2-oxopropionic acid 2-chloroethyl ester (<1% Ki67$^+$) and 2-oxopropionic acid p-tolyl ester (<1% Ki67$^+$) exhibited antiproliferative effect similar to that of EP (<1% Ki67$^+$) on corneal stroma cells activated with b-FGF, while the other derivatives had little or no effect (>30% Ki67$^+$). It is reported that correlative results for these derivatives were also obtained in a sepsis model originally described in U.S. Pat. No. 6,432,190. These two derivatives were selected for further testing for their effect on the expression of several proteins that are responsible for scar tissue formation.

Figure 19A:
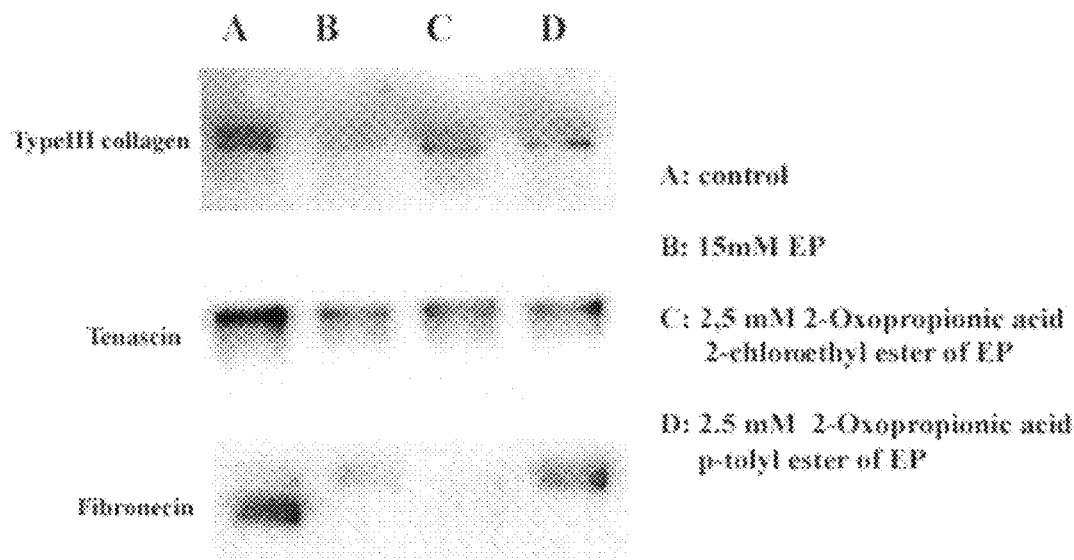
FIGS. 19A and 19B. Western blot analyses: Rabbit corneal keratocytes were isolated and cultured in serum-free DMEM/F12 into 60 mm tissue culture dishes. After 24 hrs of incubation, the media were replaced with DMEM/F12 medium containing TGF-β1 (10 ng/ml)+1% FBS without (control) or with EP or EP-derivatives for two days. The cells were extracted in RIPA buffer and the extracts containing 5 μg of total proteins were loaded per lane for Western blot analysis. Shown in FIG. 19A are reduced levels of type III collagen, tenascin and fibronectin in the cells activated in the presence of EP (B) or 2-oxopropionic acid 2-chloroethyl ester (C) and 2-oxopropionic acid p-tolyl ester (D) of EP compared to controls with no treatment (A). Also of note reduced levels of alpha-smooth muscle actin are shown in FIG. 19B, a hallmark of myofibroblasts phenotype, in the presence of EP (B) or 2-oxopropionic acid 2-chloroethyl ester (C) and 2-oxopropionic acid p-tolyl ester (D) of EP compared to controls with no treatment (A).
Figure 19B:
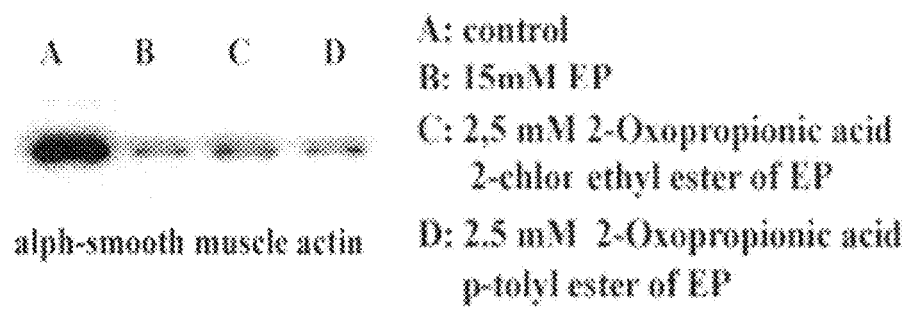

In additional experiments, it was demonstrated that there were reduced levels of type III collagen, tenascin and fibronectin in the cells activated in the presence of EP (B) or 2-oxopropionic acid 2-chloroethyl ester (C) and 2-oxopropionic acid p-tolyl ester (D) of EP compared to controls with no treatment (A) (FIG. 19A). Also there was reduced expression of alpha-smooth muscle actinin the presence of EP (B) or 2-oxopropionic acid 2-chloroethyl ester (C) and 2-oxopropionic acid p-tolyl ester (D) of EP compared to controls with no treatment (A) (FIG. 19B). The expression of alpha-smooth muscle actinin is a hallmark of myofibroblasts phenotype.

Example 4

Ethyl Pyruvate Derivative Synthesis

In certain instances, EP derivatives were chemically synthesized from pyruvic acid and an alcohol or phenol. Two methods that are useful for synthesis of the EP derivatives, acid-catalyzed condensation of the acid and the alcohol, and in situ formation of the pyruvic acid chloride and condensation of it with the alcohol or phenol in the presence of base, are given below.

2-Chloroethyl pyruvate was prepared as follows: pyruvic acid (8.8 g, 100 mmol), 2-chloroethanol (10.45 g, 130 mmol) and p-toluenesulfonic acid monohydrate (1.9 g, 10 mmol) in 40 mL of benzene were heated under reflux with azeotropic dehydration for 5 h. The mixture was cooled to room temperature and diluted with 70 mL of diethyl ether. This organic solution was washed with 100 mL of saturated aqueous NaHCO$_3$ and 100 mL of saturated aqueous NaCl. The organic layer was dried over anhydrous MgSO$_4$, filtered and solvent removed on a rotary evaporator to give 2-chloroethyl pyruvate in quantitative yield, slightly contaminated with benzene and diethyl ether (as determined by ¹H NMR). Aliquots used for biological analyses were cleared of diethyl ether and benzene by short path vacuum distillation.

tert-Butyl pyruvate was prepared as follows: tert-butyl alcohol (444 mg, 6 mmol) and pyruvic acid (528 mg, 6 mmol) were dissolved in methylene chloride (30 mL) and cooled on an ice bath. Pyridine (948 mg. 0.97 mL, 12 mmol) was added, followed by addition of 1,1-dichloromethyl methyl ether (690 mg, 0.53 mL, 6 mmol). The reaction mixture was stirred for 1 h on an ice bath, warmed to room temperature and washed with 30 mL of 5% aqueous HCl, 30 mL of saturated aqueous NaHCO$_3$, and 30 mL of saturated aqueous NaCl. The organic layer was dried over anhydrous MgSO$_4$, filtered and solvent removed on a rotary evaporator to give tert-butyl pyruvate in quantitative yield, slightly contaminated with methylene chloride (as ¹H NMR). Aliquots used for biological analyses were cleared of methylene chloride by short path vacuum distillation.

p-Tolyl pyruvate was prepared as follows. p-cresol (540 mg, 5 mmol) and pyruvic acid (440 mg, 5 mmol) were dissolved in methylene chloride (30 mL) and cooled on an ice bath. Pyridine (790 mg. 1 mL, 12.4 mmol) was added, followed by addition of 1,1-dichloromethyl methyl ether (690 mg, 0.53 mL, 6 mmol). The reaction mixture was stirred for 1 h on an ice bath, warmed to room temperature and washed with 30 mL of 5% aqueous HCl and 30 mL of saturated aqueous NaHCO$_3$. The organic layer was dried over anhydrous MgSO$_4$, filtered and solvent removed on a rotary evaporator. The residue was purified by flash silica gel chromatography (20:1→15:1 hexanes-ethyl acetate) to give 450 mg of p-tolyl pyruvate as a clear oil. ¹H NMR (400 MHZ, CDCl$_3$) δ 7.21 (d, J=4 Hz, 2H), 7.05 (d, J=4 Hz, 2H), 2.59 (s, 3H), 2.36 (s, 2H). ¹³C NMR (100 MHZ, CDCl$_3$) δ 191.3, 159.5, 148.1, 136.6, 130.4, 120.8, 27.0, 21.1. HRMS (ESI-12 Tesla FT-MS) [M+H]$^+$ calcd. 179.0708, found 179.0709.

We claim:

1. A method of inhibiting scar formation comprising topically administering to an ocular wound in a subject a composition comprising an ester of an alpha-ketoalkanoic acid chosen from one or more of ethyl pyruvate, propyl pyruvate, butyl pyruvate, carboxymethyl pyruvate, acetoxymethyl pyruvate, carbethoxymethyl pyruvate, ethoxymethyl pyruvate, 2-oxopropionic acid 3-methoxyphenyl ester, 2-oxopropionic acid 2-ethoxyethyl ester, 2-oxopropionic acid 2-chloroethyl ester, 2-oxopropionic acid isopropyl ester, 2-oxopropionic acid butyl ester, 2-oxopropionic acid p-tolyl ester, and 2-oxopropionic acid tert-butyl ester in an amount effective to inhibit a fibrotic response in the patient.

2. The method of claim 1, wherein the ocular wound is a corneal wound.

3. The method of claim 1, wherein the composition further comprises one or both of an antibiotic agent and an anti-inflammatory agent.

4. A method of ameliorating ocular fibrosis comprising topically administering an ester of an alpha-ketoalkanoic acid chosen from one or more of ethyl pyruvate, propyl pyruvate, butyl pyruvate, carboxymethyl pyruvate, acetoxymethyl pyruvate, carbethoxymethyl pyruvate, ethoxymethyl pyruvate, 2-oxopropionic acid 3-methoxyphenyl ester, 2-oxopropionic acid 2-ethoxyethyl ester, 2-oxopropionic acid 2-chloroethyl ester, 2-oxopropionic acid isopropyl ester, 2-oxopropionic acid butyl ester, 2-oxopropionic acid p-tolyl ester, and 2-oxopropionic acid tert-butyl ester in an amount effective to inhibit a fibrotic response in the patient in a pharmaceutically-acceptable carrier to an eye having a mechanical injury.

5. The method of claim 4, wherein the ester of an alpha-ketoalkanoic acid is ethyl pyruvate.

6. The method of claim 4, wherein the mechanical injury is LASIK (laser in situ keratomeliusis)-induced or PRK (photorefractive keratectomy)-induced.

7. The method of claim 4, wherein injury is a corneal injury.

8. The method of claim 4, wherein the composition further comprises one or both of an antibiotic agent and an anti-inflammatory agent.

* * * * *

SEQUENCE LISTING

<160> NUMBER OF SEQ ID NOS: 4

<210> SEQ ID NO 1
<211> LENGTH: 1126
<212> TYPE: DNA
<213> ORGANISM: Homo sapiens

<400> SEQUENCE: 1

```
gtggcgaggg cggtgcctgg gggcaggggc ctcctcggag ggcggcgggg acagacccgt      60
cgccccggct ccgcagcccc gccccggccc cgcctccgct ccggccgccg aaggctataa     120
gatctaggaa cccgagccgg tggtagggcg ggcgcggacc gtgctgggag cggcgcggct     180
ggagcgcagc gccgaaggga ctggcagggc tgaagtgtgc gggacagcaa gccccgaat     240 agccccggct gccacctcgc aggacccaag gccacgcgcg ccgggcccag ctgagccgcc     300
tcatgaagcc gcccgcggcg cagggcagcc ccgcggccgc cgcggccgca gccccggccc     360
tggactcggc ggccgcggag gacctgtcgg acgcgctgtg cgagtttgac gcggtgctgg     420
ccgacttcgc gtcgcccttc cacgagcgcc acttccacta cgaggagcac ctggagcgca     480
tgaagcggcg cagcagcgcc agtgtcagcg acagcagcgg cttcagcgac tcggagagtg     540
cagattcact ttataggaac agcttcagct tcagtgatga aaaactgaat tctccaacag     600
actctacccc agctcttctc tctgccactg tcactcctca gaaagctaaa ttaggagaca     660
caaaagagct agaagccttc attgctgatc ttgacaaaac tttagcaagt atgtgaaaca     720
agaagttctg ggtcctttca tcataaggga gaagcttcag aaagttccga ggacctgcta     780
aaatcagcta ctagaatctg ctgccagagg ggacaaagac gtgcactcaa ccttctacca     840
ggccactctc aggctcacct taaaatcagc ccttgatccc atttctgggc aatttagaca     900
gtgaaactga ctttgtttac ctgcttgcag catattagaa cagacgatcc atgctaatat     960
tgtattttct cttaaaacat agctttcctg taatttaaag tgcttttatg aaaatatttg    1020
taattaatta tatatagttg gaaatagcag taagcttttcc cattataata tatttttgta   1080
tacaaataaa atttgaactg aagtctgcaa aaaaaaaaaa aaaaaa                    1126
```

<210> SEQ ID NO 2
<211> LENGTH: 1550
<212> TYPE: DNA
<213> ORGANISM: Homo sapiens

<400> SEQUENCE: 2

```
tcaacgcctg cctcccctcg agcgtcctca gcgcagccgc cgcccgcgga gccagcacga    60
acgagcccag caccggccgg atggagcgtc gcaacccgac agcatgccc caggatttgt    120 cagaggccct gaaggaggcc accaaggagg tgcacaccca ggcagagaat gctgagttca    180
tgaggaactt tcagaagggc caggtgaccc gagacggctt caagctggtg atggcctccc    240
tgtaccacat ctatgtggcc ctggaggagg agattgagcg caacaaggag agcccagtct    300
tcgcccctgt ctacttccca gaagagctgc accgcaaggc tgccctggag caggacctgg    360
ccttctggta cgggccccgc tggcaggagg tcatccccta cacaccagcc atgcagcgct    420
atgtgaagcg gctccacgag gtggggcgca cagagcccga gctgctggtg gcccacgcct    480
acacccgcta cctgggtgac ctgtctgggg gccaggtgct caaaaagatt gcccagaaag    540
ccctggacct gccagctct ggcgagggcc tggccttctt caccttcccc aacattgcca    600
gtgccaccaa gttcaagcag ctctaccgct cccgcatgaa ctccctggag atgactcccg    660
cagtcaggca gagggtgata gaagaggcca agactgcgtt cctgctcaac atccagctct    720
ttgaggagtt gcaggagctg ctgacccatg acaccaagga ccagagcccc tcacgggcac    780
cagggcttcg ccagcggggcc agcaacaaag tgcaagattc tgcccccgtg gagactccca    840
gagggaagcc cccactcaac acccgctccc aggctccgct tctccgatgg gtccttacac    900
tcagctttct ggtggcgaca gttgctgtag ggctttatgc catgtgaatg caggcatgct    960
ggctcccagg gccatgaact tgtccggtg aaggccttc ttctagaga gggaattctc   1020 ttggctggct tccttaccgt gggcactgaa ggctttcagg gcctccagcc ctctcactgt   1080
gtccctctct ctgaaaagga ggaaggagcc tatggcatct tccccaacga aaagcacatc   1140
caggcaatgg cctaaacttc agaggggggcg aaggggtcag ccctgccctt cagcatcctc   1200
agttcctgca gcagagcctg gaagacaccc taatgtggca gctgtctcaa acctccaaaa   1260
gccctgagtt tcaagtatcc ttgttgacac ggccatgacc actttccccg tgggccatgg   1320 caattttac acaaacctga aaagatgttg tgtcttgtgt ttttgtctta tttttgttgg   1380
agccactctg ttcctggctc agcctcaaat gcagtatttt tgttgtgttc tgttgttttt   1440
atagcagggt tggggtggtt tttgagccat gcgtgggtgg ggagggaggt gtttaacggc   1500
actgtggcct tggtctaact tttgtgtgaa ataataaaca acattgtctg           1550
```

<210> SEQ ID NO 3
<211> LENGTH: 1220
<212> TYPE: DNA
<213> ORGANISM: Homo sapiens

<400> SEQUENCE: 3

```
agtcccagct cagagccgca acctgcacag ccatgcccgg gcaagaactc aggacggtga    60
atggctctca gatgctcctg gtgttgctgg tgctctcgtg gctgccgcat gggggcgccc   120
tgtctctggc cgaggcgagc cgcgcaagtt cccgggacc ctcagagttg cactccgaag   180
actccagatt ccgagagttg cggaaacgct acgaggacct gctaaccagg ctgcgggcca   240
accagagctg ggaagattcg aacaccgacc tcgtcccggc ccctgcagtc cggatactca   300
cgccagaagt gcggctggga tccggcgccc acctgcacct cgtatctct cgggccgccc   360 ttccccgaggg gctccccgag gcctcccgcc ttcaccgggc tctgttccgg ctgtccccga   420
cggcgtcaag gtcgtgggac gtgacacgac cgctgcggcg tcagctcagc cttgcaagac   480
cccaggcgcc cgcgctgcac ctgcgactgt cgccgccgcc gtcgcagtcg gaccaactgc   540
tggcagaatc ttcgtccgca cggccccagc tggagttgca cttgcggccg caagccgcca   600
```

```
gggggcgccg cagagcgcgt gcgcgcaacg gggaccactg tccgctcggg cccgggcgtt      660
gctgccgtct gcacacggtc cgcgcgtcgc tggaagacct gggctgggcc gattgggtgc      720
tgtcgccacg ggaggtgcaa gtgaccatgt gcatcggcgc gtgcccgagc cagttccggg      780
cggcaaacat gcacgcgcag atcaagacga gcctgcaccg cctgaagccc gacacggtgc      840
cagcgccctg ctgcgtgccc gccagctaca atcccatggt gctcattcaa aagaccgaca      900
ccggggtgtc gctccagacc tatgatgact tgttagccaa agactgccac tgcatatgag      960
cagtcctggt ccttccactg tgcacctgcg cggaggacgc gacctcagtt gtcctgccct     1020
gtggaatggg ctcaaggttc ctgagacacc cgattcctgc ccaaacagct gtatttatat     1080
aagtctgtta tttattatta atttattggg gtgaccttct tggggactcg ggggctggtc     1140
tgatggaact gtgtatttat ttaaaactct ggtgataaaa ataaagctgt ctgaactgtt     1200
aaaaaaaaaa aaaaaaaaa                                                   1220

<210> SEQ ID NO 4
<211> LENGTH: 2469
<212> TYPE: DNA
<213> ORGANISM: Homo sapiens

<400> SEQUENCE: 4
gacagagcaa gactctgtct caaaaaaaaa aaaaaaaga gcaaattttt tttccaaggt       60
gatagggaga gtccgtggct gatgtctgca ctgaccagac gccccctaggg ggccagcgag    120 ggcgggtccc aggtgcagcg gatgcagagg agagaggccc gggcgcggcg cggggatgg     180 tgcgatcccg ggcccgaggg catcagacgg cggctgatta gctccggttt gcatcacccg     240
gaccggggga ttagctccgg tttgcatcac ccggaccggg ggattagctc cggtttgcat     300
cacccggacc gggggccggg cgcgcacgag actcgcagcg gaagtggagg cggctccgcg     360
cgcgtccgct gctaggaccc gggcagggct ggagctgggc tgggatcccg agctcggcag     420
cagcgcagcg ggccggccca cctgctggtg ccctggaggc tctgagcccc ggcggcgccc     480
gggcccacgc ggaacgacgg ggcgagatgc gagccacccc tctggctgct cctgcgggtt     540
ccctgtccag gaagaagcgg ttggagttgg atgacaactt agataccgag cgtcccgtcc     600
agaaacgagc tcgaagtggg ccccagccca gactgccccc ctgcctgttg ccctgagcc     660 cacctactgc tccagatcgt gcaactgctg tggccactgc ctcccgtctt gggccctatg     720
tcctcctgga gcccgaggag ggcgggcggg cctaccaggc cctgcactgc cctacaggca     780
ctgagtatac ctgcaaggtg taccccgtcc aggaagccct ggccgtgctg gagcccctatg    840 cgcggctgcc cccgcacaag catgtggctc ggcccactga ggtcctggct ggtacccagc     900
tcctctacgc cttttttcact cggacccatg ggacatgca cagcctggtg cgaagccgcc     960
accgtatccc tgagcctgag gctgccgtgc tcttccgcca gatggccacc gccctggcgc    1020
actgtcacca gcacggtctg gtcctgcgtg atctcaagct gtgtcgcttt gtcttcgctg    1080
accgtgagag gaagaagctg gtgctggaga acctggagga ctcctgcgtg ctgactgggc    1140
cagatgattc cctgtgggac aagcacgcgt gcccagccta cgtgggacct gagatactca    1200
gctcacgggc ctcatactcg ggcaaggcag ccgatgtctg gagcctgggc gtggcgctct    1260
tcaccatgct ggccggccac tacccccttcc aggactcgga gcctgtcctg ctcttcggca    1320
agatccgccg cggggcctac gccttgcctg caggcctctc ggcccctgcc cgctgtctgg    1380
ttcgctgcct ccttcgtcgg gagccagctg aacggctcac agccacaggc atcctcctgc    1440
```

-continued

```
acccctggct gcgacaggac ccgatgccct tagccccaac ccgatcccat ctctgggagg    1500
ctgcccaggt ggtccctgat ggactggggc tggacgaagc cagggaagag gagggagaca    1560
gagaagtggt tctgtatggc taggaccacc ctactacacg ctcagctgcc aacagtggat    1620
tgagtttggg ggtagctcca agccttctcc tgcctctgaa ctgagccaaa ccttcagtgc    1680
cttccagaag ggagaaaggc agaagcctgt gtggagtgtg ctgtgtacac atctgctttg    1740
ttccacacac atgcagttcc tgcttgggtg cttatcaggt gccaagccct gttctcggtg    1800
ctgggagtac agcagtgagc aaaggagaca atattccctg ctcacagaga tgacaaactg    1860
gcatccttga gctgacaaca cttttccatg accataggtc actgtctaca ctgggtacac    1920
tttgtaccag tgtcggcctc cactgatgct ggtgctcagg cacctctgtc caaggacaat    1980 cccttcaca  aacaaaccag ctgcctttgt atcttgtacc ttttcagaga aagggaggta    2040
tccctgtgcc aaaggctcca ggcctctccc ctgcaactca ggacccaagc ccagctcact    2100
ctgggaactg tgttcccagc atctctgtcc tcttgattaa gagattctcc ttccaggcct    2160
aagcctggga tttgggccag agataagaat ccaaactatg aggctagttc ttgtctaact    2220
caagactgtt ctggaatgag ggtccaggcc tgtcaaccat ggggcttctg acctgagcac    2280
caaggttgag ggacaggatt aggcagggtc tgtcctgtgg ccacctggaa agtcccaggt    2340
gggactcttc tggggacact tggggtccac aatcccaggt ccatactcta ggttttggat    2400
accatgagta tgtatgttta cctgtgccta ataaggaga  attatgaaat aaaaaaaaaa    2460
aaaaaaaaa                                                            2469
```